(12) United States Patent
Chou et al.

(10) Patent No.: US 7,759,090 B2
(45) Date of Patent: Jul. 20, 2010

(54) EXPRESSION SYSTEM FOR PRODUCING COLLAGEN

(75) Inventors: Min-Yuan Chou, Taipei Hsien (TW);
Hsiu-Chuan Li, Hsinchu County (TW);
Chuan-Chuan Huang, Taipei County (TW)

(73) Assignee: Industrial Technology Research Institute, Hsinchu (TW)

( * ) Notice: Subject to any disclaimer, the term of this patent is extended or adjusted under 35 U.S.C. 154(b) by 217 days.

(21) Appl. No.: 11/889,607

(22) Filed: Aug. 15, 2007

(65) Prior Publication Data

US 2009/0030184 A1 Jan. 29, 2009

Related U.S. Application Data

(62) Division of application No. 11/250,391, filed on Oct. 17, 2005, now Pat. No. 7,279,329.

(51) Int. Cl.
*C12P 21/06* (2006.01)
*C12N 15/00* (2006.01)
*C12N 9/06* (2006.01)
*C12N 5/07* (2006.01)
*C12N 1/20* (2006.01)
*C07K 1/00* (2006.01)
*C07H 21/00* (2006.01)

(52) U.S. Cl. .................. 435/69.1; 435/320.1; 435/191; 435/348; 435/252.3; 530/356; 536/23.5

(58) Field of Classification Search ........................ None
See application file for complete search history.

(56) References Cited

U.S. PATENT DOCUMENTS

| 5,077,214 | A | 12/1991 | Guarino et al. |
| 5,593,859 | A | 1/1997 | Prockop et al. |
| 5,637,477 | A | 6/1997 | Spaulding et al. |
| 6,428,978 | B1 | 8/2002 | Olsen et al. |

OTHER PUBLICATIONS

Whisstock et al. Quaterly Reviews of Biophysics, 2003, "Prediction of protein function from protein sequence and structure", 36(3): 307-340.*
Chica et al. Semi-rational approaches to engineering enzyme activity: combining the benefits of directed evolution and rational design, Curr Opin Biotechnol. Aug. 2005;16(4):378-84. Review.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Pihlajaniemi et al., The EMBO Journal vol. 6 No. 3 pp. 643-649, 1987.
Berg et al., vol. 52, No. 1, 1973, Biochemical and Biophysical Research Communications, pp. 115-120.
Rosenbloom et al., Archives of Biochemistry and Biophysics 158, pp. 478-484 (1973).
Kivirikko et al., The FASEB Journal, vol. 3, Mar. 1989, pp. 1609-1617.
Prockop et al., Annu. Rev. Biochem. 1995. 64:403-34.
Koivu et al., The Journal of Biological Chemistry, vol. 262, No. 14, Issue of May 15, pp. 6447-6449, 1987.
John et al., Biochem J. (1996) 317, pp. 659-665.
Wagner et al., Biochem J. (2000) 352, pp. 907-911.
Toman et al., The Journal of Biological Chemistry, vol. 275, No. 30, Issue of Jul. 28, pp. 23303-23309, 2000.
Veijola et al., Biochem J. (1996) 315, pp. 613-618.
Holden et al., The Journal of Biological Chemistry, vol. 276, No. 8, Issue of Feb. 23, pp. 6046-6055, 2001.
Keene et al., The Journal of Cell Biology, vol. 113, No. 4, May 1991, pp. 971-978.
Montserret et al., Biochemistry, vol. 38, No. 20, 1999, pp. 6479-6488.
Pihlajamaa et al., The Journal of Biological Chemistry, vol. 279, No. 23, Issue of Jun. 4, pp. 24264-24273, 2004.
Mazzorana et al., The Journal of Biological Chemistry, vol. 276, No. 30, Issue of Jul. 27, 27989-27998, 2001.
Chou et al., Genomics vol. 79, No. 3, Mar. 2002, pp. 395-401.
Fitzgerald et al., FEBS Letters 505 (2001) 275-280.
Broeck et al., Journal of Neurochemistry, vol. 64, No. 6, 1995, pp. 2387-2395.
Tuckwell, Matrix Biology 21 (2002) 63-66.
Lamberg et al., The Journal of Biological Chemistry, vol. 271, No. 20, Issue of May 17, pp. 11988-11995, 1996.
Myllyharju et al., The Journal of Biological Chemistry, vol. 272, No. 35, Issue of Aug. 29, pp. 21824-21830, 1997.
Nokelainen et al., Matrix Biology vol. 16/1997/98, pp. 329-338.
Pihlajamaa et al., The Journal of Biological Chemistry, vol. 274, No. 32, Issue of Aug. 6, pp. 22464-22468, 1999.
Nagata, TIBS 21, Jan. 1996, pp. 23-26.
Bruick et al. A conserved family of prolyl-hydroxylases that modify HIF. Science. Nov. 9, 2001;294(5545):1337-40. Epub Oct. 11, 2001.
GenBank Accession No. M24487, Human prolyl 4-hydroxylase alpha subunit mRNA, complete cds, clone PA-15, created Apr. 27, 1993.
GenBank Accession No. X05130, Human mRNA for prolyl 4-hydroxylase beta subunit (EC 1.14.11.2) (procollagen-L-proline, 2-oxoglutarate:oxygen oxidoreductase, 4-hyroxylating, created Mar. 30, 1995.

* cited by examiner

*Primary Examiner*—Richard Hutson
*Assistant Examiner*—Iqbal H Chowdhury
(74) *Attorney, Agent, or Firm*—Birch, Stewart, Kolasch & Birch, LLP

(57) ABSTRACT

A DNA molecule consisting of the nucleotide sequence of SEQ ID NO: 1, which encodes a collagenous (COL1) domain and a C-terminal noncollagenous (NC1) domain of type XXI collagen. Expression systems and methods for the expression of the DNA molecule are also provided.

8 Claims, 10 Drawing Sheets

NC2 — COL1 — NC1

MKAFCITFTAVVAFVGLSHG RSIPG PPGPIGPEGPRGLPGLPGRDGVPGLV
GVPGRPGVRGLKGLPGRNGEKGSQGFGYPGEQGPPGPEGPPGISKE
GPPGDPLPGKDGDHGKPGIQGQPGPPGIC DPSLCFSVIARRDPFRKGP
NYSLDDSSHHHHHHSSG

FIG. 2A

EXPRESSION SYSTEM FOR PRODUCING COLLAGEN

This application is a Divisional of application Ser. No. 11/250,391, filed on Oct. 17, 2005 now U.S. Pat. No. 7,279,329, the entire contents of which are hereby incorporated by reference and for which priority is claimed under 35 U.S.C. §120.

BACKGROUND

The invention relates to expression systems for producing collagen; more particularly, the invention relates to co-expression of collagen and prolyl 4-hydroxylase in stably transfected insect cells.

Collagens are extracellular matrix proteins that contain the repeating triplet sequence Gly-X-Y and the presence of such triplets allows three collagen polypeptide chains (α-chains) to fold into a triple-helical conformation. The Y position amino acid in the triplet sequence Gly-X-Y is frequently proline, which is often 4-hydroxylated by post-translational modification of the collagen polypeptide chain in order to stabilize the triple-helical structure of collagen. In the absence of proline hydroxylation, the essential triple helical conformation of collagen is thermally unstable at below physiological temperatures (Berg, R. A., and Prockop, D. J. (1973) Biochem Biophys Res Commun 52, 115-120; Rosenbloom, J., et al. (1973) Arch Biochem Biophys 158, 478-484). Prolyl 4-hydroxylase (EC 1.14.11.2), the key enzyme catalyzing the 4-hydroxylation of proline residues in all collagens, from vertebrates is an $\alpha_2\beta_2$ tetramer consisting of two different types of subunits (Kivirikko, K. I., et al., (1989) Faseb J3, 1609-1617). The α subunit contains the catalytic and peptide-substrate binding domains but is inactive in the absence of the β subunit. The β subunit was found to be identical to the enzyme protein-disulfide isomerase (Koivu, J., et al. (1987) J Biol Chem 262, 6447-6449; and Pihlajaniemi, T., et al. (1987) Embo J6, 643-649). During collagen biosynthesis, the procollagen α chains are co-translationally transported into the lumen of the endoplasmic reticulum where they are hydroxylated by prolyl 4-hydroxylase. Prolyl 4-hydroxylase requires $Fe^{2+}$, 2-oxoglutarate, $O_2$ and ascorbate, and an active system appears to exist in vertebrate cells for the transport of 2-oxoglutarate and ascorbate into the lumen of the endoplasmic reticulum (Kivirikko, K. I., et al. (1989) Faseb J3, 1609-1617). In vitro expression of an active recombinant prolyl 4-hydroxylase from its subunits has been successfully obtained by co-infection of insect cells *Spodoptera frugiperda* and *Trichoplusia ni* (Vuori, K., et al. (1992) Proc Natl Acad Sci USA 89, 7467-7470) with recombinant baculoviruses, or cotransfection with expression vectors in mammalian cell lines COS-1 (John, D. C., and Bulleid, N. J. (1996) Biochem J 317 (Pt 3), 659-665) and HEK293 (Wagner, K., et al. (2000) Biochem J352 Pt 3, 907-911), in yeasts *Pichia pastoris* (Vuorela, A., et al. (1997) Embo J16, 6702-6712) and *Saccharomyces cerevisiae* (Toman, P. D., et al. (2000) J Biol Chem 275, 23303-23309). The prolyl 4-hydroxylase tetramer assembly probably requires molecular chaperones, such as immunoglobulin heavy chain binding protein, BiP (John, D. C., and Bulleid, N. J. (1996) Biochem J 317 (Pt 3), 659-665; Veijola, J., et al. (1996) Biochem J315 (Pt 2), 613-618).

Expression systems for producing recombinant collagens in the present includes *E. coli*, yeast, mammalian cell lines, insect cells, as well as transgenic animals and plants, however, these expression systems have their own disadvantages. For example, *E. coli* expression system has no post-translational modification, and yeast expression system lacks prolyl 4-hydroxylase activity, through the yield of collagens in *Pichia pastoris* was the highest among these expression systems. Mammalian cell line expression system has low yield and limits to specific tissue types, and insect cell expression system has low prolyl 4-hydroxylase activity. As for transgenic animals, such as silk worm or mice, or plant, such as tobacco, the collagen products were overly cross-linked. A baculovirus expression system containing genes encoding human prolyl 4-hydroxylase and collagen has been established (U.S. Pat. Nos. 5,077,214 and 5,593,859), however, the transfected insect cells will be destroyed in 72 hours, resulting in only transient recombinant protein production. In addition, it is difficult to recover or purify the recombinant collagens because of cell lysis. Moreover, collagens are secreted or membrane proteins, and the destruction of endoplasmic reticulum or Golgi body by the baculovirus limits the production of collagens. An expression system for producing biologically active collagens in high yield is, therefore, still required.

SUMMARY

The inventors established stable insect cell lines producing the α and β subunits of P4H (human prolyl 4-hydroxylase) in both *Trichoplusia ni* and *Drosophila melanogaster* S2 expression systems. Type XXI minicollagen comprising the intact C-terminal noncollagenous (NC1) and collagenous domain (COL1) was used as a model to characterize the collagen structure and chain assembly in the *Drosophila* system by coexpression of the three genes in a stably transformed manner. The invention is, thus, achieved.

Accordingly, an embodiment of the invention provides a recombinant insect cell. The recombinant cell includes a transfected gene encoding human prolyl 4-hydroxylase. The recombinant cell further includes a DNA molecule consisting of the nucleotide sequence of SEQ ID NO: 1. The DNA molecule encodes a collagenous (COL1) domain and a C-terminal noncollagenous (NC1) domain of type XXI collagen. The cell can be a *Trichoplusia ni* cell or a *Drosophila melanogaster* cell.

Another embodiment of the invention provides a method for producing a recombinant collagen. The method includes the steps of providing a recombinant insect cell including a transfected gene encoding human prolyl 4-hydroxylase; transfected an expression vector comprising a recombinant collagen gene into the cell; culturing the cell under conditions such that the recombinant collagen gene is expressed; and recovering the expressed recombinant collagen.

Yet another embodiment of the invention provides a method for producing a recombinant collagen. The method includes the steps of: providing a recombinant insect cell comprising a transfected gene encoding recombinant collagen, and a transfected gene encoding prolyl 4-hydroxylase; culturing the recombinant insect cell under conditions such that the recombinant collagen is expressed; and recovering the expressed recombinant collagen.

The other embodiment of the invention provides a DNA molecule consisting of the nucleotide sequence of SEQ ID NO: 1. The DNA molecule encodes a collagenous (COL1) domain and a C-terminal noncollagenous (NC1) domain of type XXI collagen. A recombinant collagen encoded the DNA molecule is also provided.

BRIEF DESCRIPTION OF THE DRAWINGS

Embodiments of the invention can be more fully understood and further advantages become apparent when reference is made to the following description and the accompanying drawings in which:

FIGS. 2A and 2B illustrate Contribution of human prolyl 4-hydroxylase in the assembly of type XXI minicollagen in *Drosophila* S2 cells. FIG. 2A illustrates the predicted primary sequence of recombinant mC21 (SEQ ID NO:2). The *Drosophila* expression construct pMT/BiP-mC21 contains the sequences encoding the *Drosophila* BiP signal sequence (shaded area), the last four amino acid residues of the NC2 domain, the entire COL1 and NC1 domains of human α1(XXI) collagen, and a C-terminal histidine tag. The predicted N-terminus after cleavage of the signal peptide is indicated by the downward pointing arrow. Prolyl residues predicted to be hydroxylated are indicated by a large dot. The FACIT collagen family characteristic two GXY imperfections and the two cysteinyl residues at the COL1/NC1 junction involved in interchain disulfide bridging are indicated in italic and boldface, respectively. FIG. 2B illustrates Western blot analysis of mC21 molecules expressed in *Drosophila* S2 cells. The culture media from the stably transfected *Drosophila* cells 120 h post-induction with $Cu^{2+}$ was electrophoresed on a 10% SDS/Bis-Tris polyacrylamide gel with MES buffer under non-reducing (lanes 1 and 2) and reducing (lane 3) conditions and then immunoblotted with a monoclonal antibody to the C-terminal of type XXI collagen, 3E2. Lane 1, the culture media of *Drosophila* cells stably transfected with mC21 alone (mC21ΔP4H); Lanes 2 and 3, the culture media of *Drosophila* cells coexpressing P4Hα, P4Hβ and mC21 (mC21/P4H). T, interchain disulfide-bonded trimers; D, interchain disulfide-bonded dimers; M, monomers.

DETAILED DESCRIPTION

Figure 1A:
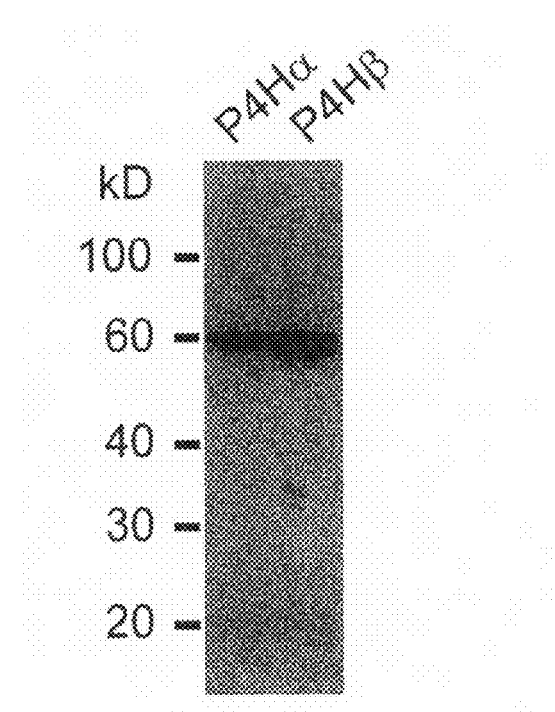
FIGS. 1A and 1B illustrate Western blot analyses of the soluble protein extract of *Trichoplusia ni* (A) and *Drosophila* S2 (B) cells harboring the stably transfected P4Hα and P4Hβ expression constructs. The P4H stably transfected *Drosophila* S2 cells were either cultured alone (B, lanes 1 and 3) or induced with 0.5 mM of copper sulfate and kept growing for 120 h before harvesting (B, lanes 2 and 4). The cells were broken in a buffer containing 0.2% Triton X-100 and about 50 μg of soluble cell extract were used for immunoblotting.

A recombinant collagen and a DNA molecule corresponding thereto, a recombinant insect cell including a transfected gene encoding a human prolyl hydroxylase, and a method for producing the recombinant collagen using the recombinant insect cell are provided.

Twenty-seven distinct types of homo- and heterotrimeric molecules, encoded by more than 42 genes, have been identified in vertebrates. These proteins exhibit considerable diversity in size, sequences, tissue distribution, molecular composition and each plays a different structural role in connective tissue. Triple-helical assembly of fibrillar collagens (collagen types I, II, III, V, and XI) is initiated by association of their conserved large C-terminal non-triple-helical domains (around 250 amine acids), called the C-propeptides, and then folded into a triple-helix by propagation of the three α chains from the C to N termini (Prockop, D. J., and Kivirikko, K. I. (1995) Annu Rev Biochem 64, 403-434). The FACIT (fibril-associated collagen with interrupted triple-helices) collagen family, including types IX, XII, XIV, XVI, XIX, XX, XXI and XXII, is a group of nonfibrillar collagens and some of them have been shown to connect to collagen fibrils and interact with other matrix components or cells (Fukai, N., et al. (1994) Methods in Enzymology 245, 3-28; Holden, P., Meadows, R. S., et al. (2000) J Biol Chem; Keene, D. R., Lunstrum, G. P., et al. (1991) J Cell Bio 113, 971-978; Montserret, R., et al. (1999) Biochemistry 38, 6479-6488; Pihlajamaa, T., et al. (2004) J Biol Chem 279, 24265-24273). The FACIT collagens are devoid of large C-propeptides, which are replaced by significantly shorter C-terminal non triple-helical domains (NC1). The NC1 domains of the FAC-ITs do not share any sequence similarity. In contrast, FACITs display remarkable similarities in their NC1 adjacent triple-helical domains (COL1) and the junction of the COL1 and NC1 domains, including two cysteines separated by four amino acids are responsible for interchain disulfide bonding. Previous studies on the assembly of recombinant minicollagen XII using the baculovirus expression system show that folding of the triple-helical COL1 domain precedes the formation of the disulfide bonds (Mazzorana, M., et al. (2001) J Biol Chem 276, 27989-27998).

The α1(XXI) collagen (α1-chain of type XXI collagen) encodes a protein of 957 amino acid residues and possesses a putative 22-residue signal peptide and 2 COL domains interspersed with 3 NC regions. The inventors' previous study indicated that type XXI collagen is an extracellular matrix component of the blood vessel walls and the expression is developmentally regulated (Chou, M. Y., and Li, H. C. (2002) Genomics 79, 395-401). So far, type XXI collagen has mainly been characterized at the cDNA and genomic levels (Chou, M. Y., and Li, H. C. (2002) Genomics 79, 395-401; Fitzgerald, J., and Bateman, J. F. (2001) FEBS Lett 505, 275-280; Tuckwell, D. (2002) Matrix Biol 21, 63-66), while studies at the protein level have been hampered by its low level of expression and the lack of suitable antibodies. Expression of the α1(XXI) collagen chain recombinantly may provide an alternative approach to study the structure and function of type XXI collagen.

*Drosophila* Schneider 2 (S2) cells derived from *Drosophila melanogaster* have been developed as a plasmid-based insect cell system (Schneider, I. (1972) J Embryol Exp Morphol 27, 353-365). In the plasmid-based non-lytic expression system, rather than using recombinant baculovirus, high copy numbers of recombinant plasmid vectors have been shown to be inserted into the host cell genome, with the advantage that foreign proteins are expressed continuously and stably without destroying cells (Vanden Broeck, J., et al. (1995) J Neurochem 64, 2387-2395; and Johansen, H., et al. (1989) Genes Dev 3, 882-889).

The inventor established stably transfected insect cell lines containing cDNAs encoding the α and β subunits of human prolyl 4-hydroxylase in both *Trichoplusia ni* and *Drosophila melanogaster* S2 cells. The involvement of prolyl 4-hydroxylase in the assembly of the three alpha chains to form trimeric type XXI minicollagen, which comprises the intact C-terminal noncollagenous (NC1) and collagenous domain (COL1), in the *Drosophila* system were further characterized. When minicollagen XXI was stably expressed in *Drosophila* S2 cells alone, negligible amounts of interchain disulfide-bonded trimers were detected in the culture media. However, minicollagen XXI was secreted as disulfide-bonded homotrimers by coexpression with prolyl 4-hydroxylase in the stably transfected *Drosophila* S2 cells. Minicollagen XXI coexpressed with prolyl 4-hydroxylase contained sufficient amounts of hydroxyproline to form thermally stable pepsin-resistant triple helices consisting of both interchain and non-interchain disulfide-bonded trimers. These results demonstrate that a sufficient amount of active prolyl 4-hydroxylase is required for the assembly of type XXI collagen triple helices in *Drosophila* cells and the trimeric assembly is governed by the C-terminal collagenous domain.

Accordingly, one embodiment of the invention provides a recombinant insect cell including a transfected gene encoding prolyl 4-hydroxylase. The transfected gene includes α subunit and/or β subunit of prolyl 4-hydroxylase. The α subunit of prolyl 4-hydroxylase includes the nucleotide sequence of SEQ ID NO: 3, and the β subunit of prolyl 4-hydroxylase includes the nucleotide sequence of SEQ ID NO: 5. The recombinant insect cell further includes a transfected gene encodes a collagenous (COL1) domain and a C-terminal noncollagenous (NC1) domain of type XXI collagen, including the nucleotide sequence of SEQ ID NO: 1.

In the embodiment of the recombinant insect cell of the invention, the cell can be a *Trichoplusia ni* cell or a *Drosophila melanogaster* cell, preferably, *Drosophila melanogaster* cell.

Another embodiment of the invention provides a method for producing a recombinant collagen. The method includes the steps of: providing a recombinant insect cell; transfecting an expression vector comprising a recombinant collagen gene into the cell; culturing the cell under conditions such that the recombinant collagen gene is expressed; and recovering the expressed recombinant collagen.

In the embodiment of the method for producing a recombinant collagen, the recombinant insect cell including a transfected gene encoding human prolyl 4-hydroxylase. Specifically, the transfected gene includes α subunit and/or β subunit of prolyl 4-hydroxylase. The α subunit of prolyl 4-hydroxylase includes the nucleotide sequence of SEQ ID NO: 3, and the β subunit of prolyl 4-hydroxylase includes the nucleotide sequence of SEQ ID NO: 5. The recombinant cell can be a *Trichoplusia ni* cell or a *Drosophila melanogaster* cell.

In another embodiment of the method for producing a recombinant collagen, the recombinant collagen gene encodes a collagenous (COL1) domain and a C-terminal noncollagenous (NC1) domain of type XXI collagen, including the nucleotide sequence of SEQ ID NO: 1. The expressed recombinant collagen is secreted.

Yet another embodiment of the invention provides a method for producing a recombinant collagen. The method includes the steps of: providing a recombinant insect cell comprising a transfected gene encoding recombinant collagen, and a transfected gene encoding prolyl 4-hydroxylase; culturing the recombinant insect cell under conditions such that the recombinant collagen is expressed; and recovering the expressed recombinant collagen.

In one embodiment of the method for producing a recombinant collagen, the recombinant collagen gene encodes a collagenous (COL1) domain and a C-terminal noncollagenous (NC1) domain of type XXI collagen, including the nucleotide sequence of SEQ ID NO: 1. The expressed recombinant collagen is secreted.

In the other embodiment of the method for producing a recombinant collagen, the transfected gene encoding prolyl 4-hydroxylase includes α subunit and/or β subunit of prolyl 4-hydroxylase. The α subunit of prolyl 4-hydroxylase includes the nucleotide sequence of SEQ ID NO: 3, and the β subunit of prolyl 4-hydroxylase includes the nucleotide sequence of SEQ ID NO: 5.

In another embodiment of the method for producing a recombinant collagen, the insect cell can be a *Trichoplusia ni* cell or a *Drosophila melanogaster* cell, preferably a *Drosophila melanogaster* cell.

The other embodiment of the invention provides a DNA molecule consisting of the nucleotide sequence of SEQ ID NO: 1. The DNA molecule encodes a collagenous (COL1) domain and a C-terminal noncollagenous (NC1) domain of type XXI collagen. A recombinant collagen encoded by the DNA molecule is also provided.

Co-expression of collagen genes and cDNAs encoding the two subunits of prolyl 4-hydroxylase in insect lepidopteran cells, including *Spodoptera frugiperda* and *Trichoplusia ni* using the baculovirus infection system has lead to the synthesis of completely hydroxylated, thermally stable collagens (Lamberg, A., et al. (1996) J Biol Chem 271, 11988-11995; Hagg, P. M., et al. (1997) Am J Pathol 150, 2075-2086; Myllyharju, J., et al. (1997) J Biol Chem 272, 21824-21830; Nokelainen, M., et al. (1998) Matrix Biol 16, 329-338; Pihlajamaa, T., et al. (1999) J Biol Chem 274, 22464-22468). However, a disadvantage of the baculovirus system is that cells are ultimately destroyed by the infected viruses, resulting in only transient recombinant protein production. In the invention, non-lytic insect expression systems both in *Trichoplusia ni* and *Drosophila* S2 cells were established to facilitate the downstream process of recombinant collagen production. Since prolyl 4-hydroxylase is the key enzyme of collagen biosynthesis, a high expression level of functional prolyl 4-hydroxylase in these stably transfected insect cell systems would ensure a success in trimeric assembly of collagen chains afterward. The results of the examples showed that the total activity of prolyl 4-hydroxylase in the P4H stably transfected *Trichoplusia ni* cells increased only 2-fold as compared with the endogenous enzyme in the non-transfected cell control. One possible explanation for the low expression level of P4H could be that the expression of P4H under the control of OpIE2 promoter, an immediate-early gene of *Orgyia pseudotsugata* multicapsid nuclear polyhedrosis virus, is significant lower than that of polyhedrin or P10 promoters which were used in the baculovirus infection system. In contrast, the protein expression levels of both subunits of P4Hα and P4Hβ, as well as the total activity of prolyl 4-hydroxylase, coexpressed in the *Drosophila* S2 inducible system were 3~4-fold higher than that in the *Trichoplusia ni* system, probably due to high copy numbers of recombinant plasmid vectors that were inserted into the genome of *Drosophila* S2 cells. The 2-oxoglutarate enzymatic assays confirmed that the stably transfected *Drosophila* S2 system can produce functional recombinant P4H. The subsequent results in the trimeric assembly of mC21 further proved that the P4H was functionally active for prolyl hydroxylation of the collagen chains and formation of stable triple-helical structure. These data suggest that the P4Hα and P4Hβ are capable of assembling into an active $\alpha_2\beta_2$ tetramer in the *Drosophila* expression system.

It is the first time to produce recombinant collagen using a three-gene expression system in the *Drosophila melanogaster* cells. In addition, the results of the examples provide the first biochemical evidence for triple helix formation of a recombinant human type XXI minicollagen molecule and its capability to form disulfide-linked polymers only in the presence of enough active prolyl 4-hydroxylase in *Drosophila* S2 cells. Based on the results from mass spectrometric analysis, there were still considerable amounts of under-hydroxylated proline residues present in the mC21 that had been coexpressed with P4H. Since *Drosophila* S2 cells can not survive below a cell density of $2 \times 10^5$ cells/ml (Echalier, G. (1997) *Drosophila* cells in culture, Chapters 2 and 3, Academic Press, New York), it is difficult to select a single stable clone in which all three gene expression constructs of mC21, P4Hα and P4Hβ co-exist. Thus, the established stably transfected polyclonal cell population may contain cells possessing only mC21 construct, along with an antibiotic selection vector. It is, therefore, that the purified mC21 from the P4H coexpressed stable *Drosophila* S2 cells may contain under-hydroxylated collagen molecules. The presence of pepsin-resistant, non-interchain disulfide-bonded mC21 triple helices indicated that the trimeric assembly of type XXI collagen may be initiated from the COL1 domain and disulfide bridging of the two-cysteine residues in the junction of COL1/NC1 domains was not a prerequisite for initiating the triple-helical structure formation. This is in agreement with the previous studies on the assembly of recombinant minicollagen XII using the baculovirus expression system showing that folding of the triple-helical COL1 domain precedes the formation of the disulfide bonds (Mazzorana, M., et al. (2001) J Biol Chem 276, 27989-27998). The data of the examples showed that the formation of interchain disulfide-bonded minicollagen XXI trimer is dependent on hydroxyproline content of collagen chains, suggesting that the triple-helical assembly governs fine formation of the interchain disulfide bridges.

The inventors have proved that it is possible to produce active recombinant human prolyl 4-hydroxylase and collagen molecules with stable triple helices in the *Drosophila* S2 cell expression system. Furthermore, this non-lytic insect cell system would seem to provide an easy way for studying the mechanisms involved in the assembly of collagen triple helix, especially for those collagens that are expressed in cells and tissues in the amount too low to be characterized at the protein level. It was found shown that both P4H and mC21 can be produced in the *Drosophila* S2 cell line constitutively, indicating that the *Drosophila* S2 cell expression system can be used for the production of various recombinant collagen types for numerous scientific and medical purposes.

Practical examples are described herein.

EXAMPLES

Example 1

Production of Monoclonal Antibody of α1(XXI) Collagen

For the production of C-terminal monoclonal antibody of α1(XXI) collagen, a synthetic peptide corresponding to residues 936-957 (CDPSLCFSVIARRDPFRKGPNY) (residues 128-149 of SEQ ID NO:2) in the NC1 domain of human type XXI collagen was synthesized (AnaSpec, Inc). Two milligrams of purified peptide were conjugated to keyhole limpet hemocyanin (Pierce). The coupled peptide solution was emulsified in ImmunEasy (Qiagen) and injected intradermally into two mice for monoclonal antibodies production following standard procedures (Harlow, E., and Lane, D. (1988) Antibodies: a laboratory manual, Cold Spring Harbor Laboratory, Cold Spring Harbor, N.Y.). The hybridoma 3E2 was selected for this study and the total IgG was purified from media on a protein G column according to the standard protocol.

Example 2

Construction of Recombinant Plasmids

The open reading frames coding for the α and β subunits of human prolyl 4-hydroxylase genes were amplified by RT-PCR from human aortic smooth muscle cells (Clonetics). For the expression of prolyl 4-hydroxylase in the non-lytic insect cell expression system, both the InsectSelect™ and *Droso-* phila inducible expression (DES®) systems (Invitrogen) were used. In the InsectSelect™ system, the cDNAs coding for the α and β subunits of human prolyl 4-hydroxylase were cloned at the KpnI-XhoI, and the KpnI-XbaI sites of the expression vector pIZ/V5-His, and were named pIZ/P4Hα and pIZ/P4Hβ, respectively. Both the α and β subunits of human prolyl 4-hydroxylase gene expressions were under the control of OpIE2 promoter derived from the baculovirus *Orgyia pseudotsugata* multicapsid nuclear polyhedrosis virus. The expression cassette of the α subunit of human prolyl 4-hydroxylase gene in pIZ/P4Hα construct was PCR amplified with primers ATCGATTATCATGTCTGGA (SEQ ID NO: 7) and CTTTGAGTGAGCATCGATC (SEQ ID NO: 8) and then was subcloned into the pIZ/P4Hβ at Cla I site. The resulting construct was named pIZ/P4H. In the *Drosophila* inducible expression system, the cDNAs coding for the α and β subunits of human prolyl 4-hydroxylase were cloned at the NcoI-XhoI, and the PstI-XbaI sites of the expression vector pMT/V5-HisA, and were named pMT/P4Hα and pMT/P4Hβ, respectively. Both the α and β subunits of human prolyl 4-hydroxylase gene expressions were under the control of metallothionein promoter, which is inducible by addition of copper or cadmium ions.

DNA constructs for the expression of mC21 in *Drosophila* S2 cells were obtained as follows. DNA corresponding to nucleotides 2484-2874 of the COL21A1 open reading frame was cloned by PCR amplification with primers 5'-TTA-GATCTATTCCTGGGCCACCTGGTCCGATAG-3' (SEQ ID NO: 9) and 5'-AATCTAGACTAATAGTTTGGTC-CTTTTCTG-3' (SEQ ID NO: 10). The PCR product was digested with BglII and XbaI, followed by cloning into the expression vector pMT/BiP-V5-HisA (Invitrogen) at the same sites. The resulting construct was named pMT/BiP-mC21.

Example 3

Establishment of Stably Transfected Insect Cell Lines Expression P4H

Expression of P4H in non-lytic insect cell expression systems both in *Trichoplusia ni* and *Drosophila* S2 cells were described below.

(1) In *Trichoplusia ni* Cells

In the InsectSelect™ System, *Trichoplusia ni* cells (High Five, Invitrogen) were transfected with pIZ/P4H using Superfect transfection reagent (Qiagan). After transfection, zeocine-resistant cells were selected at a final concentration of 400 μg/ml for 4 weeks. Ten well-isolated colonies from the antibiotic-resistant clones were picked and the protein expression levels of both P4Hα and P4Hβ from the cell lysates of each stable clones were examined by Western blot analysis with monoclonal antibodies against P4Hα and P4Hβ (purchased from ICN, Ins.), respectively. Western blot analysis was as described below. SDS-PAGE was carried out using a 10% NuPAGE bis-Tris polyacrylamide gel with morpholineethanesulfonic acid (MES) buffer (Invitrogen) and proteins were stained with Simple Blue Safestain reagent (Invitrogen). After SDS-PAGE, proteins were transferred to a nitrocellulose membrane. The membrane was blocked with 5% nonfat milk in PBS containing 0.1% Tween-20 and probed with antibodies. The bound antibodies were detected with peroxidase-conjugated secondary antibodies and visualized by the SuperSignal detection reagent (Pierce). The X-ray films were scanned using a densitometer for quantitation. One of the clones showing the highest expression level of P4Hα was chosen for further studies.

Comparison of the P4Hα and P4Hβ expression levels in the *Trichoplusia ni* cell lysates showed that the protein expression level of P4Hα is approximately 5 times less than P4Hβ (FIG. 1A).

(2) In *Drosophila* S2 Cells

Figure 1B:
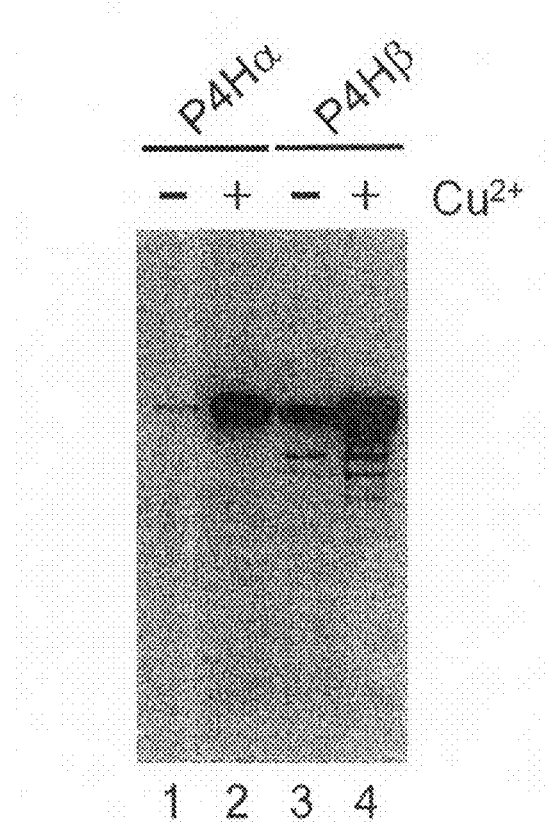

For the expression of P4H in the *Drosophila* inducible expression system, *Drosophila* S2 cells were co-transfected with pMT/P4Hα, pMT/P4Hβ, and pCoHygro at a ratio of 10:10:1 using Effectene transfection reagent (Qiagen). After transfection, hygromycin B-resistant cells were selected at a final concentration of 300 μg/ml for 4 weeks. The expression of both P4Hα and P4Hβ is driven by the metallothionein promoter which is inducible by addition of copper ions. After addition of 0.5 mM of copper sulfate into the cultured cells and cells were kept growing for 120 h, both P4Hα and P4Hβ protein expression levels were increased dramatically as compared to the non-induced controls (FIG. 1B).

To examine whether the recombinant P4H produced in the above non-lytic insect systems are functionally active, the enzymatic activities of P4H expressed in the *Trichoplusia ni* and *Drosophila* S2 cells were assayed by using a method based on the decarboxylation of 2-oxo[1-$^{14}$C]glutarate (Kivirikko, K. I., and Myllyla, R. (1982) Methods Enzymol. 82, 245-304). The results were shown in TABLE I.

TABLE I

Assays for recombinant prolyl 4-hydroxylase activity in *Trichoplusia ni* and *Drosophila* S2 cells

| Cell lysate | Prolyl 4-hydroxylase activity[a] |
|---|---|
| 100 μg[b] | Dpm |
| *Trichoplusia ni* cells | |
| Non-transfected control | 55 ± 15 |
| P4H-transfected | 101 ± 24 |
| *Drosophila* S2 cells | |
| Non-transfected control | 172 ± 22 |
| P4H-transfected, uninduced | 271 ± 23 |
| P4H-transfected, Cu$^{2+}$ induced | 356 ± 37 |

[a]The assay is based on the hydroxylation-coupled decarboxylation of 2-oxo[1-$^{14}$C]glutarate with a synthetic peptide (GPP)$_{10}$ as substrate.
[b]Cells were broken in a buffer containing 0.2% Triton X-100 and about 100 μg of soluble cell extract were used in each assay. P4H-transfected *Drosophila* cells were harvested 120 h post-induction.

As shown in TABLE I, *Trichoplusia ni* cells alone contained trace amount of endogenous prolyl 4-hydroxylase activity as reported previously (Lamberg, A., et al. (1996) J Biol Chem 271, 11988-11995). The P4H activity in the stably transfected cell line increased less than 2-fold as compared with the endogenous enzyme in the non-transfected cell control. Interestingly, with the same amounts of soluble cellular proteins, the endogenous prolyl 4-hydroxylase activity in the *Drosophila* S2 cells is 1.7-fold higher than the P4H transfected *Trichoplusia ni* stable clone. The P4H activity in both non-induced and Cu$^{2+}$-induced *Drosophila* S2 cell line that had been stably transfected with P4H increased around 1.6- and 2-fold than the non-transfected control, respectively. The results indicated that the *Drosophila* S2 system is better than the *Trichoplusia ni* system for expressing recombinant P4H in a non-lytic mariner. Therefore, the *Drosophila* S2 system was chosen for the subsequent studies of minicollagen XXI expression.

Example 4

Recombinant Expression of mC21

In the beginning, it is our attempt to express full-length α1(XXI) collagen in both *Trichoplusia ni* and *Drosophila* S2 cell systems harboring the above stably-transformed P4H genes. Unfortunately, Western blot analysis of the recombinant collagen products in both systems using antibodies against α1(XXI) collagen revealed that the full-length α1(XXI) collagen molecule was degraded into several distinct fragments (data not shown). Previous studies in the trimeric assembly of chicken minicollagen XII demonstrated that the triple helical structure formation is initiated at the C-terminal collagenous domain (Mazzorana, M., et al. (2001) J Biol Chem 276, 27989-27998). In order to see whether the C-terminal collagenous domain in α1(XXI) collagen molecule is capable of initiating trimeric assembly of functional triple helical structure, mC21 comprising the intact C-terminal noncollagenous (NC1) and collagenous domain (COL1) was expressed in Drosophila S2 cells.

FIG. 2A illustrates the predicted primary sequence of recombinant mC21. The Drosophila expression construct pMT/BiP-mC21 contains the sequences encoding the Drosophila BiP signal sequence (shaded area) in the N-terminal of mC21 for secretion purpose, the last four amino acid residues of the NC2 domain, the entire COL1 and NC1 domains of human α1(XXI) collagen, and a C-terminal histidine tag. The predicted N-terminus after cleavage of the signal peptide is indicated by the downward pointing arrow. Prolyl residues in the Y position of an XYG triplet sequence and thus predicted to be hydroxylated (Kivirikko, K. I., et al. (1992) In Post-Translational Modifications of Proteins (Harding, J. J., and Crabbe, M. J. C., Eds.) CRC Press, Boca Raton, Fla., 1-51) are indicated by a large dot. The FACIT collagen family characteristic two GXY imperfections and the two cysteinyl residues at the COL1/NC1 junction involved in interchain disulfide bridging are indicated in italic and boldface, respectively.

For the expression of mC21, pMT/BiP-mC21 was co-transfected with pCoBlast vector into Drosophila S2 cells or the stable clone that bearing functional P4H. In the Drosophila S2 system, because S2 cells do not survive below a cell density of $2 \times 10^5$ cells/ml, it was not a feasible approach to select a single colony from a plate for expansion. All colonies from one plate were pooled as a stable cell line after blastcidine selection for three weeks with a final concentration of 30 μg/ml. Both cell lysate and culture media were analyzed by Western blotting with monoclonal antibody 3E2, which recognizes the C-terminal NC1 domain of α1(XXI) collagen. The results were shown in FIG. 2B. The culture media from the stably transfected Drosophila cells 120 h post-induction with $Cu^{2+}$ was electrophoresed on a 10% SDS/Bis-Tris polyacrylamide gel with MES buffer under non-reducing (lanes 1 and 2) and reducing (lane 3) conditions and then immunoblotted with a monoclonal antibody to the C-terminal of type XXI collagen, 3E2.

Figure 2B:
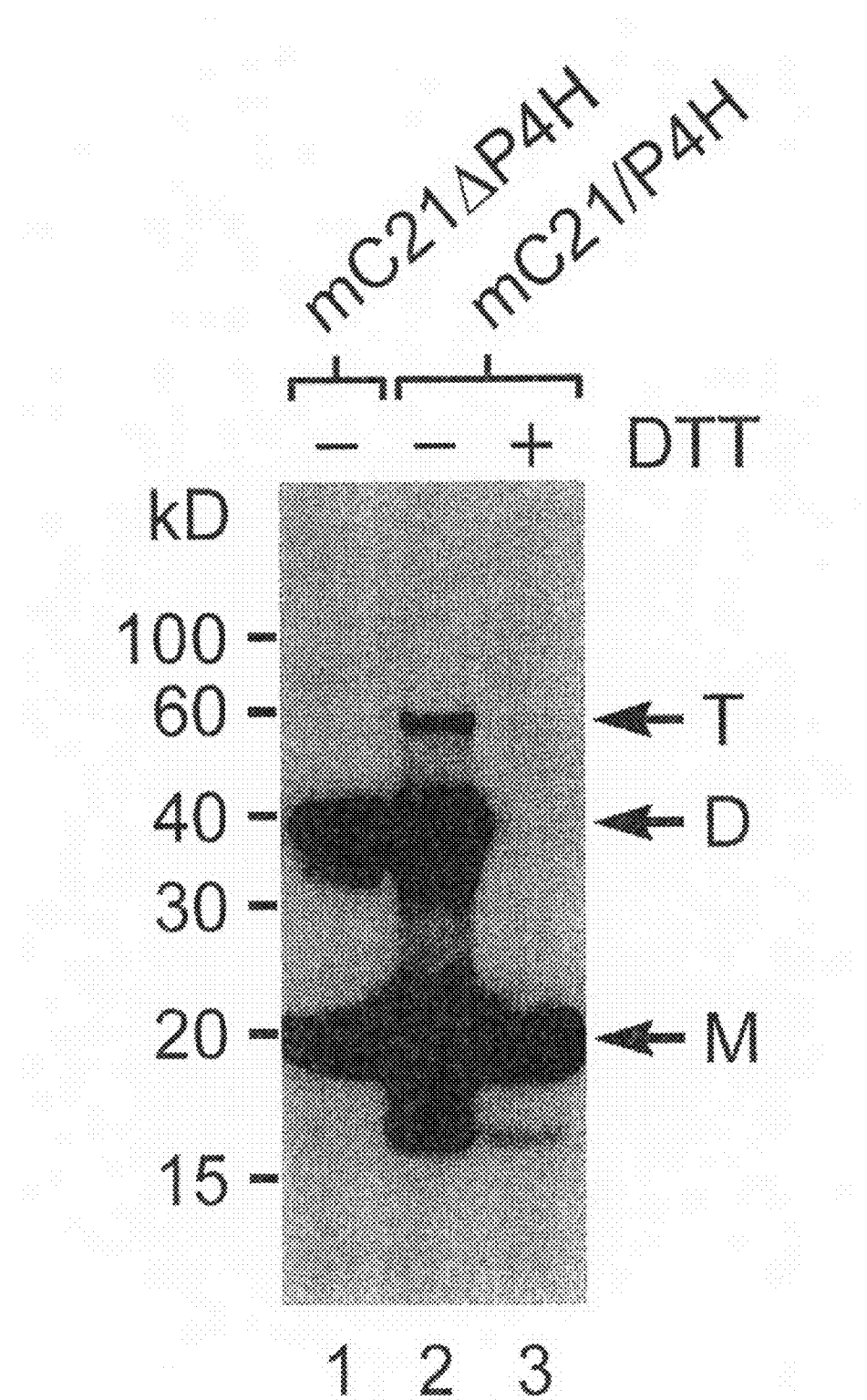

It was found that mC21 was expressed exclusively in the culture media as a soluble form, indicating that the Drosophila BiP signal sequence directed the protein secretion successfully. When mC21 was stably expressed in Drosophila alone, two major bands corresponding to the mC21 monomers and interchain disulfide-bonded dimers with apparent molecular masses of 20 and 40 kD, respectively, were detected (FIG. 2B, lane 1). However, mC21 was able to assemble as interchain disulfide-bonded homotrimers (60 kD) in the P4H stably transfected Drosophila cell line (lane 2). Reduction of mC21 produced in the P4H stably transfected Drosophila cells showed that the dimers and trimers obtained in these conditions were indeed reducible (lane 3). These results indicated that a sufficient amount of active recombinant prolyl 4-hydroxylase is required for the assembly of disulfide-bonded trimeric mC21 molecules in the Drosophila S2 cell expression system.

Example 5

Constitutive Expression of Three Human Genes in Stably Transfected Drosophila S2 Cells To examine whether the co-transfected Drosophila clone containing three genes of P4Hα, P4Hβ, and mC21 can produce recombinant proteins continuously, we carried out a 6-day time course study by Western blot analysis of each protein with the corresponding antibodies.

Figure 3:
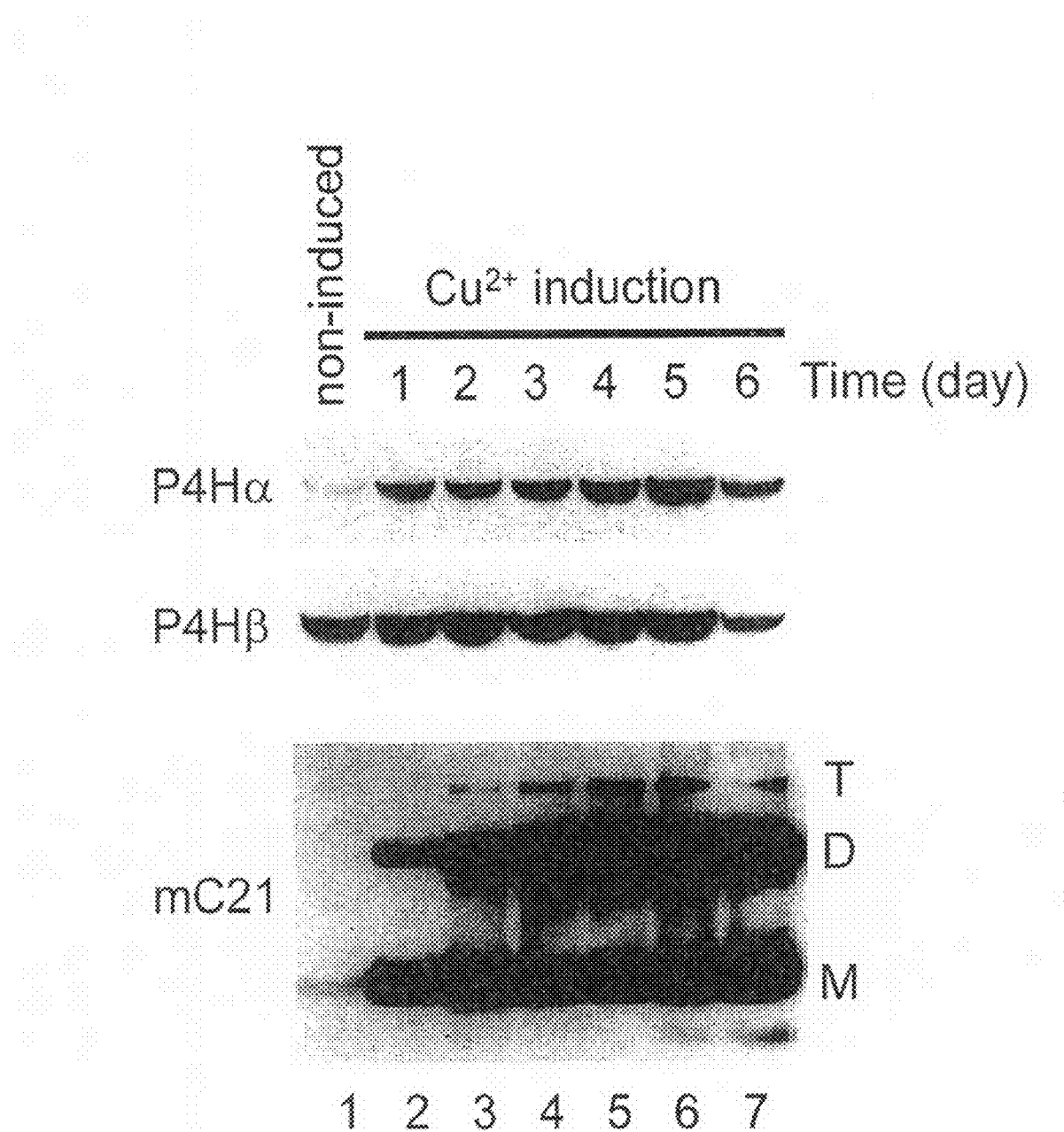
FIG. 3 illustrates time-course analysis of protein expression in *Drosophila* cells containing stably transfected P4Hα, P4Hβ, and minicollagen XXI genes. The *Drosophila* clone was induced with 0.5 mM of copper sulfate and protein expression level for P4Hα, P4Hβ, and mC21 were examined over a 6-day time course (lanes 2 to 7). Sodium ascorbate (80 μg/ml) was added everyday. Equal amounts of cellular lysate and aliquots of culture media were prepared at indicated time intervals and were used for the detection of P4Hα, P4Hβ, and mC21 expression by Western blotting with the indicated monoclonal antibodies shown on the left. Lane 1, Stably-transfected *Drosophila* S2 cells without $Cu^{2+}$ induction. T, interchain disulfide-bonded trimers; D, interchain disulfide-bonded dimers; M, monomers.

In the beginning, stably transfected mC21 and/or P4H genes were expressed in Drosophila S2 cells grown in serum free media (Hyclone) in shaker flasks. The cells were seeded at a density of $4 \times 10^6$ cells/ml and maintained at $1 \times 10^7$ cells/ml. Inducible expression of recombinant proteins was performed by addition of 0.5 mM of copper sulfate into the media and grown over different time course. Sodium ascorbate (80 μg/ml) was added to the culture media daily for those clones containing mC21 cDNA constructs. Western blotting analysis results were shown in FIG. 3. Lane 1 indicates non-induction control. The results showed that an increasing amounts of P4Hα and P4Hβ were detected from the cell lysates over 5 days of time span. The P4Hβ produced in the Drosophila stable clone reached a maximal amount on day 2 post-induction, whereas the P4Hα took 5 days to reach a full amount expression. The expression intensity of the three forms of mC21 was highest at day 5 post-induction. The interchain-disulfide bonded trimeric form of mC21 started to appear 48 h post-induction, and continued to increase until a maximum level was reached 5 days post-induction. Notably, the expression levels of P4Hα and mC21 trimers over the time course are in proportion, indicating that a significant amount of catalytic P4Hα in the Drosophila cells is required for the assembly of interchain disulfide-bonded trimer of type XXI collagen. Approximately 1 month following induction, the amounts of P4Hα, P4Hβ and mC21 produced by the stable clone at various passage levels were compared again. It was found that the expression intensities of the three genes were about the same at each passage, indicating that the Drosophila stable clone produced the three recombinant proteins steadily (data not shown).

Example 6

Characterization of Purified Recombinant Minicollagen XXI

Recombinant mC21, with and without coexpression with P4H in the Drosophila S2 cells, were purified from culture media by column chromatographies as described below.

Stably transfected Drosophila S2 cells were induced in the presence of 0.5 mM of copper sulfate for mC21 and P4H expression and cells were grown in conditioned media for 120 h at 27° C. Around 300 ml of filtered culture media containing C-terminal His-tagged minicollagen were applied to a non-charged His-Bind Fractogel column (1.5×8 cm, Novagen) equilibrated with 20 mM sodium acetate buffer, pH 6.0 at a flow rate of 60 ml/h. After washing with the same buffer, the minicollagen was eluted with 0.1 M of imidazole in the same buffer. The UV absorbance was monitored at 280 nm and peak fractions containing minicollagen were pooled and dialyzed against 20 mM sodium acetate buffer, pH 6.0 at 4° C. overnight. The dialysate was applied onto a HighTrap sulfopropyl column (1-ml in bed volume) equilibrated with 20 mM sodium acetate buffer, pH 6.0 at a flow rate of 60 ml/h. The column was first washed with 50 mM of NaCl and then the bound minicollagen was eluted with 0.25 M of NaCl in the same buffer. The peak fractions were pooled and applied onto a $ZnSO_4$-charged chelating Sepharose HighTrap column (1-ml in bed volume) equilibrated with 50 mM sodium acetate buffer containing 0.1 M NaCl, pH 6.0 at a flow rate of 60 ml/h. The column was first washed with 25 mM of imidazole and then the bound minicollagen was eluted with 0.25 M of imidazole in the same buffer. The final preparation was dialyzed against 50 mM of sodium acetate, pH 6.0. The expression level of mC21, with and without coexpression with P4H in the Drosophila S2 cells after cooper sulfate induction for 5 days, were ~3 mg/l, as estimated from the amount of purified mC21 obtained and the recovery of the purification (data not shown). Protein concentration was determined by the Lowry assay using bovine serum albumin as the standard.

Figure 4:
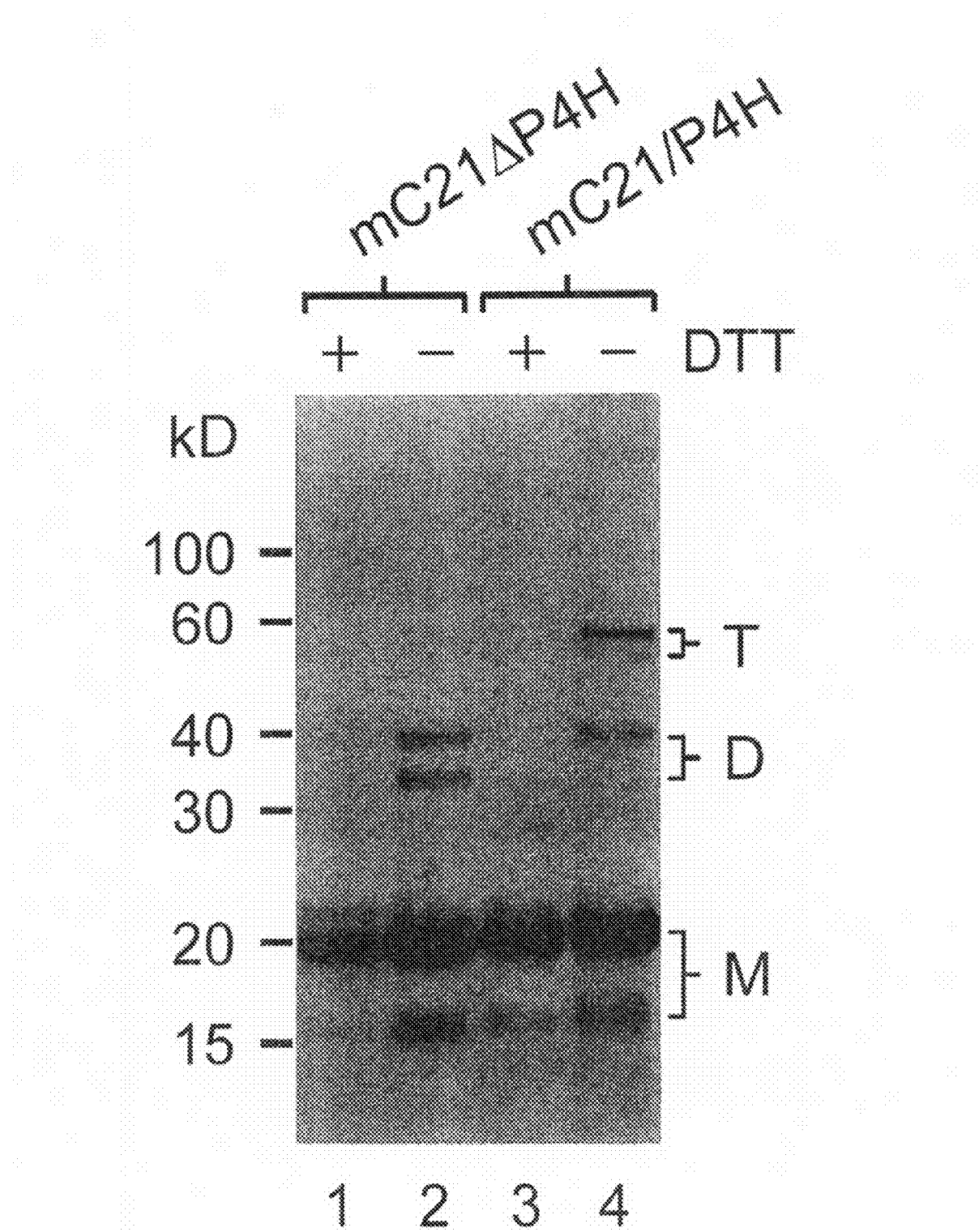
FIG. 4 illustrates purification of minicollagen XXI from the stably transfected *Drosophila* S2 cells. Recombinant mC21 expressed in *Drosophila* S2 cells alone (mC21ΔP4H) and coexpressed in the P4H stably transfected *Drosophila* S2 cells (mC21/P4H) were purified from culture media by column chromatographies. The samples were electrophoresed on a 10% SDS/Bis-Tris polyacrylamide gel with MES buffer under reducing conditions (lanes 1 and 3) and non-reducing conditions (lanes 2 and 4). The gel was stained with Simple Blue Safestain reagent. T, interchain disulfide-bonded trimers; D, interchain disulfide-bonded dimers; M, monomers.

Samples of purified recombinant mC21 were electrophoresed on 10% SDS/Bis-Tris polyacrylamide gels with MES buffer under reducing conditions (lanes 1 and 3) and no reducing conditions (lanes 2 and 4). The gel was stained with Simple Blue Safestain reagent. The results were shown in FIG. 4. Three major bands corresponding to the interchain disulfide-bonded trimeric, dimeric and non-disulfide-bonded monomeric molecules of mC21 (FIG. 4, lanes 2 and 4) migrated as doublets in SDS-PAGE under non-reducing conditions as previously observed in the Western blot in FIG. 2B. Individual protein bands from each doublets from tri-, di-, and mono-molecules were excised from SDS-polyacrylamide gels and subjected to tryptic digestion using sequencing grade trypsin (Promega) with an established procedure. Recovered peptides were analyzed by MALDI-TOF (Matrix-Assisted Laser Desorption Ionization Time-of-Flight) analysis (ABI 4700 Proteomics analyzer) for peptide mapping. No differences were detected in the molecular masses of mC21 peptide fragments between each protein doublet, indicating that the doublet may result from the retention of some secondary structure even in the presence of SDS, or as a non-interchain disulfide-bonded species (data not shown). These mC21 species were reduced into monomer doublet completely under reducing conditions (FIG. 4, lanes 1 and 3).

To directly demonstrate the presence of hydroxyprolines in the recombinant mC21, as processed by the prolyl 4-hydroxylase in the stably transfected Drosophila S2 cells, amino acid composition and mass spectrometric analyses were performed on a purified sample. For amino acid analysis, purified recombinant mC21 was dialyzed against 50 mM acetic acid, hydrolyzed in 6 N of HCl at 110° C. for 24 h and subjected to amino acid analysis in a Beckman system 6300 amino acid analyzer. The results were shown in TABLE II.

TABLE II

Amino acid analysis of the purified recombinant human minicollagen XXI without and with coexpression with human prolyl 4-hydroxylase in Drosophila S2 cells

| | Recombinant human minicollagen XXI | | |
|---|---|---|---|
| Amino acid | P4H transfected | non-P4H co-transfected[b] Residues[c] | Calculated[a] (from cDNA) |
| Asx | 9.4 ± 1.9 | 10.6 ± 0.2 | 10 |
| Glx | 14.4 ± 4.3 | 11.6 ± 0.4 | 9 |
| Hyp | 2.4 ± 0.1 | 5.5 ± 0.2 | — |
| Ser | 8.5 ± 1.8 | 9.9 ± 0.2 | 10 |
| Gly | 29.8 ± 2.9 | 27.1 ± 0.5 | 37 |
| His | 10.0 ± 1.2 | 9.5 ± 0.5 | 7 |
| Arg | 8.5 ± 0.5 | 8.9 ± 0.2 | 9 |
| Thr | 1.6 ± 0.4 | 2.0 ± 0.2 | 0 |
| Ala | 3.0 ± 0.5 | 3.5 ± 0.3 | 1 |
| Pro | 23.2 ± 1.3 | 20.3 ± 2.2 | 31 |
| Tyr | 2.9 ± 0.3 | 3.0 ± 0.3 | 2 |
| Val | 5.6 ± 0.3 | 5.3 ± 0.1 | 5 |
| Met | 0.5 ± 0.3 | 0.4 ± 0.1 | 0 |
| Cys | 1.4 ± 0.2 | 1.6 ± 0.6 | 2 |
| Ile | 5.0 ± 0.6 | 5.3 ± 0.1 | 6 |
| Leu | 7.8 ± 1.9 | 8.9 ± 0.2 | 8 |
| Phe | 4.7 ± 0.6 | 4.1 ± 0.2 | 3 |
| Lys | 7.4 ± 1.2 | 8.3 ± 0.1 | 6 |
| Hyp/Pro = | 0.10 | 0.27 | |
| % Hyp/(Hyp + Pro) = | 9 | 21 | |

[a]The calculated amino acid residues are based on the deduced amino acid sequence of mC21 after removal of the Drosophila BiP signal sequence as shown in FIG. 2A.
[b]Purified mC21 was derived from the cell media 120 h post-induction of the cells with cooper sulfate.
[c]The values are given as mean ± S.D., n = 2.

Figure 5A:
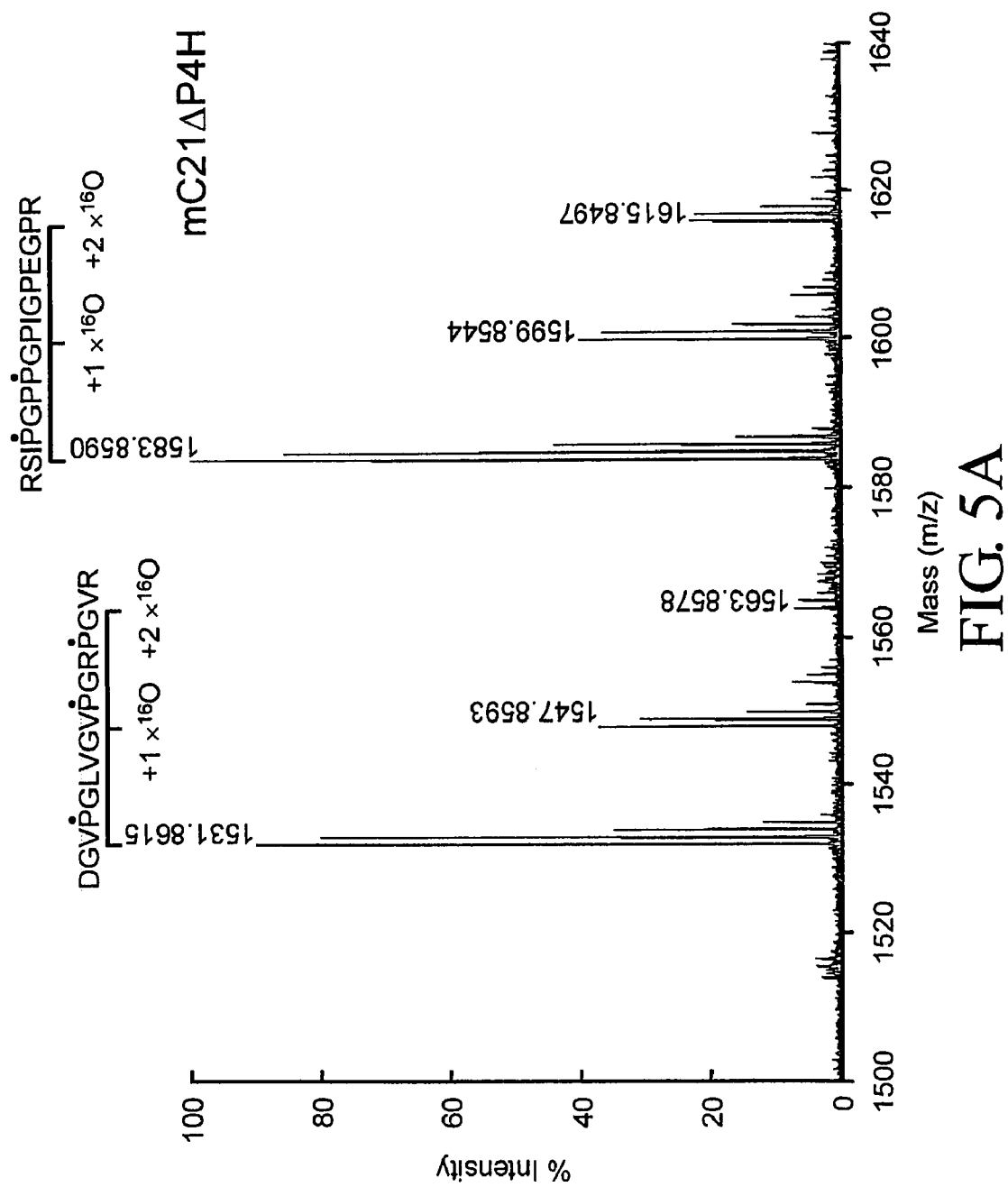
FIGS. 5A and 5B illustrate MALDI-TOF mass spectrometric analysis of the tryptic fragments (residues 43-58 and 19-34 of SEQ ID NO:2) of minicollagen XXI expressed in *Drosophila* S2 cells. Recombinant mC21, with and without coexpression with P4H in the *Drosophila* S2 cells, were electrophoresed on a 10% SDS/Bis-Tris polyacrylamide gel with MES buffer under reducing conditions. Protein bands were visualized by staining with Simple Blue Safestain reagent, followed by in-gel digestion with trypsin and MALDI-TOF mass spectrometric analysis. Two tryptic peptides derived from mC21 expressed in *Drosophila* S2 cells alone, mC21ΔP4H (A); and coexpressed in the P4H stably transfected *Drosophila* S2 cells, mC21/P4H (B) were chosen for study. Prolyl residues in the Y position of an XYG triplet sequence and thus predicted to be hydroxylated are indicated by a dot.
Figure 5B:
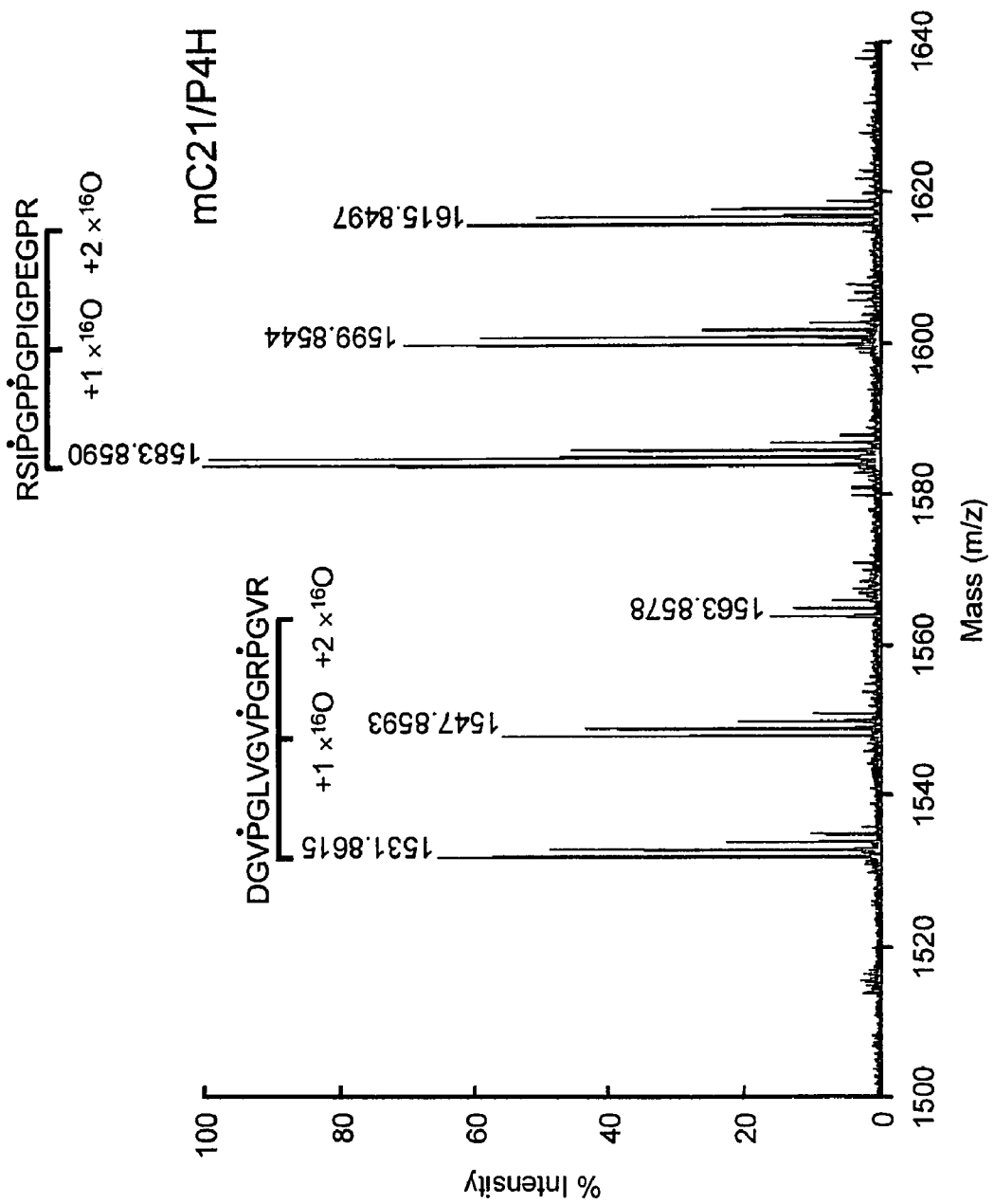

As shown in TABLE II, the amino acid compositions in the purified mC21, with and without coexpression with P4H in the Drosophila S2 cells, were in agreement with the composition expected based on its cDNA deduced amino acid sequence. The degree of hydroxylation (the ratio of hydroxyproline residues to total proline residues plus hydroxyproline residues) in mC21, without and with coexpression with P4H, was 9 and 21%, respectively. The theoretical value for the fully hydroxylated proline residues is 17 (FIG. 2A) and thus the degree of hydroxylation is 54.8%. The results may indicate that the proline residues in mC21 molecules coexpressed by the P4H stably transfected Drosophila S2 cells were not fully hydroxylated, even though the hydroxyproline content of type XXI collagen from nature source is unknown. To further examine the extent of proline hydroxylation in the mC21 polypeptide chain, the purified mC21 was subjected to trypsin digestion, followed by MALDI-TOF mass spectrometric analysis. Two tryptic peptides derived from mC21 expressed in Drosophila S2 cells alone (FIG. 5A); or coexpressed in the P4H stably transfected Drosophila S2 cells (FIG. 5B) were chosen for comparison. The peptide fragments, with and without coexpression with P4H in Drosophila S2 cells, still contain substantial fraction of unhydroxylated molecules with molecular masses of 1531.86 and 1583.86. Mono- and bi-hydroxylated peptides were also found in each of the tryptic fragments based on the additional molecular mass of oxygen atom(s) in each peptide. The relative intensities of hydroxylated versus non-hydroxylated peptide molecules in the P4H stably transfected S2 cells were substantially higher than those in the P4H non-transfected cells (FIG. 5, compare A with B), in agreement with the results from the amino acid composition analysis of overall minicollagen molecules.

Example 7

Triple-Helical Conformation of Minicollagen XXI

Figure 6:
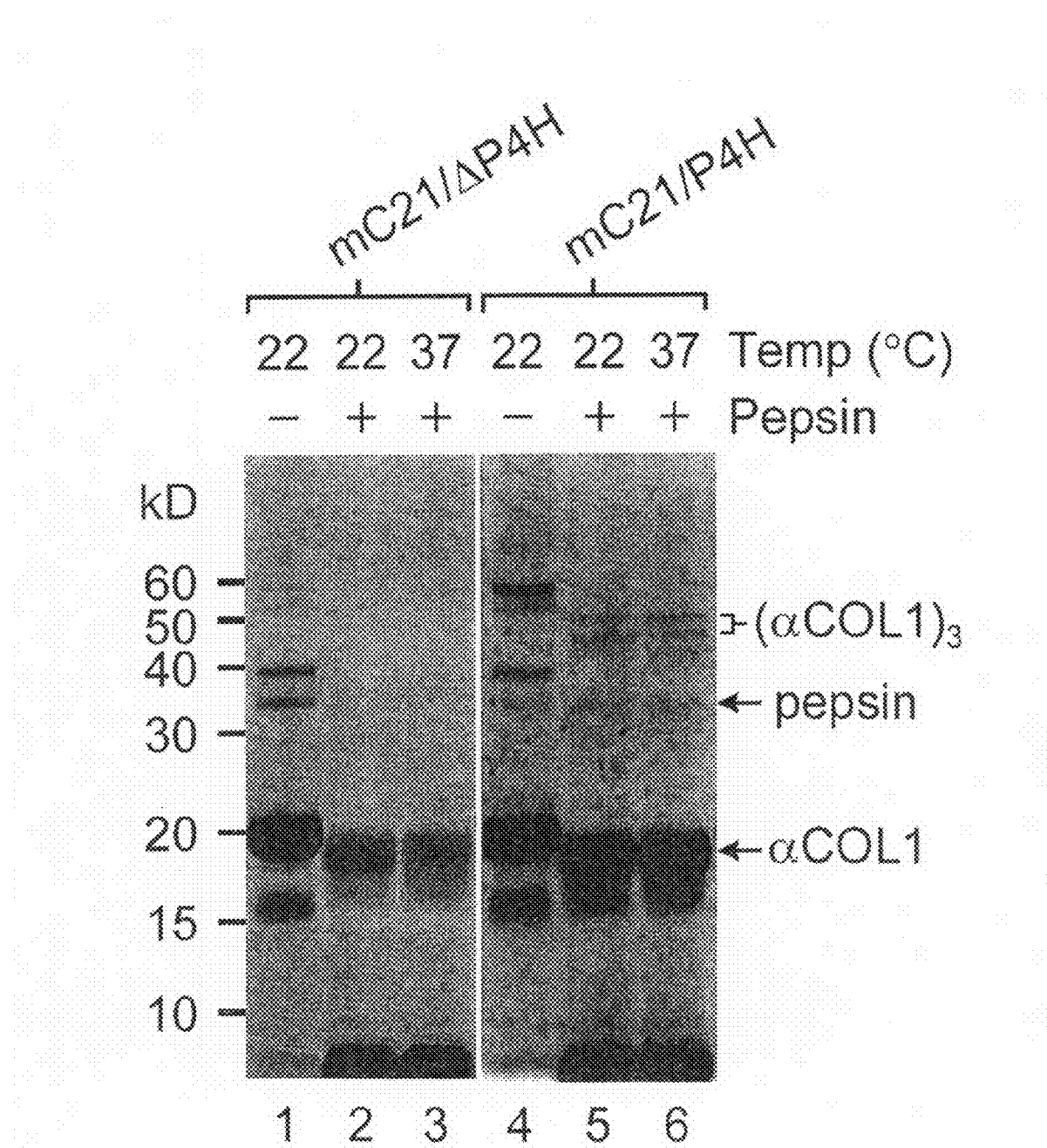
FIG. 6 illustrates characterization of the triple-helical structure of minicollagen XXI. Purified recombinant mC21, expressed in *Drosophila* S2 cells alone (mC21ΔP4H) and coexpressed in the P4H stably transfected *Drosophila* S2 cells (mC21/P4H), were incubated for 15 min at 22° C. (lanes 2 and 5) and 37° C. (lanes 3 and 6) and then treated with pepsin for 2 h at 22° C. Pepsin digested minicollagens were electrophoresed on a 10% SDS/Bis-Tris polyacrylamide gel with MES buffer under non-reducing conditions, and proteins were visualized by Coomassie staining. Lanes 1 and 4, undigested recombinant minicollagens XXI, mC21ΔP4H and mC21/P4H, respectively. Pepsin is indicated by the arrow. $(\alpha COL1)_3$, trimeric disulfide-bonded COL1 domain; (αCOL1), isolated chains dissociated from trimeric non-disulfide-bonded COL 1 domain.

Collagen triple-helices are resistant to pepsin degradation. To determine whether the COL1 domain of mC21 is in triple-helical conformation, purified mC21, with and without coexpression with P4H, were adjusted to pH 2.5 with 0.5 M of acetic acid, incubated at 22° C. and 37° C. for 15 min, followed by pepsin (25 µg/ml) digestion for 2 h to access helical stability. If mC21 is in a triple-helical conformation, pepsin digestion should lead to the removal of its NC1 domain and production of COL1 domain with the two cysteines present at the COL1/NC1 junction. As shown in FIG. 6, when mC21 was expressed in Drosophila alone, the entire interchain disulfide-bonded dimers and most monomers were disappeared after pepsin digestion at either temperature point (lanes 2 and 3), indicating that the proline residues in most of the mC21 molecules were under-hydroxylated and no triple-helical structure was formed. In contrast, some pepsin-resistant fragments derived from interchain disulfide-bonded trimers, (αCOL1)₃, and monomers (αCOL1) were remained following pepsin digestion of mC21 that had been coexpressed with P4H (lane 5). Moreover, these fragments were still existed when mC21 was pre-incubated at 37° C. (lane 6) followed by digestion with pepsin, suggesting that some of the mC21 molecules coexpressed in the P4H stably transfected Drosophila cells contained sufficient amounts of hydroxyprolines to stabilize the triple-helical structure. These pepsinization results demonstrated that coexpression of mC21 with P4H in Drosophila cells is capable of forming thermally stable triple-helical conformation.

Figure 7A:
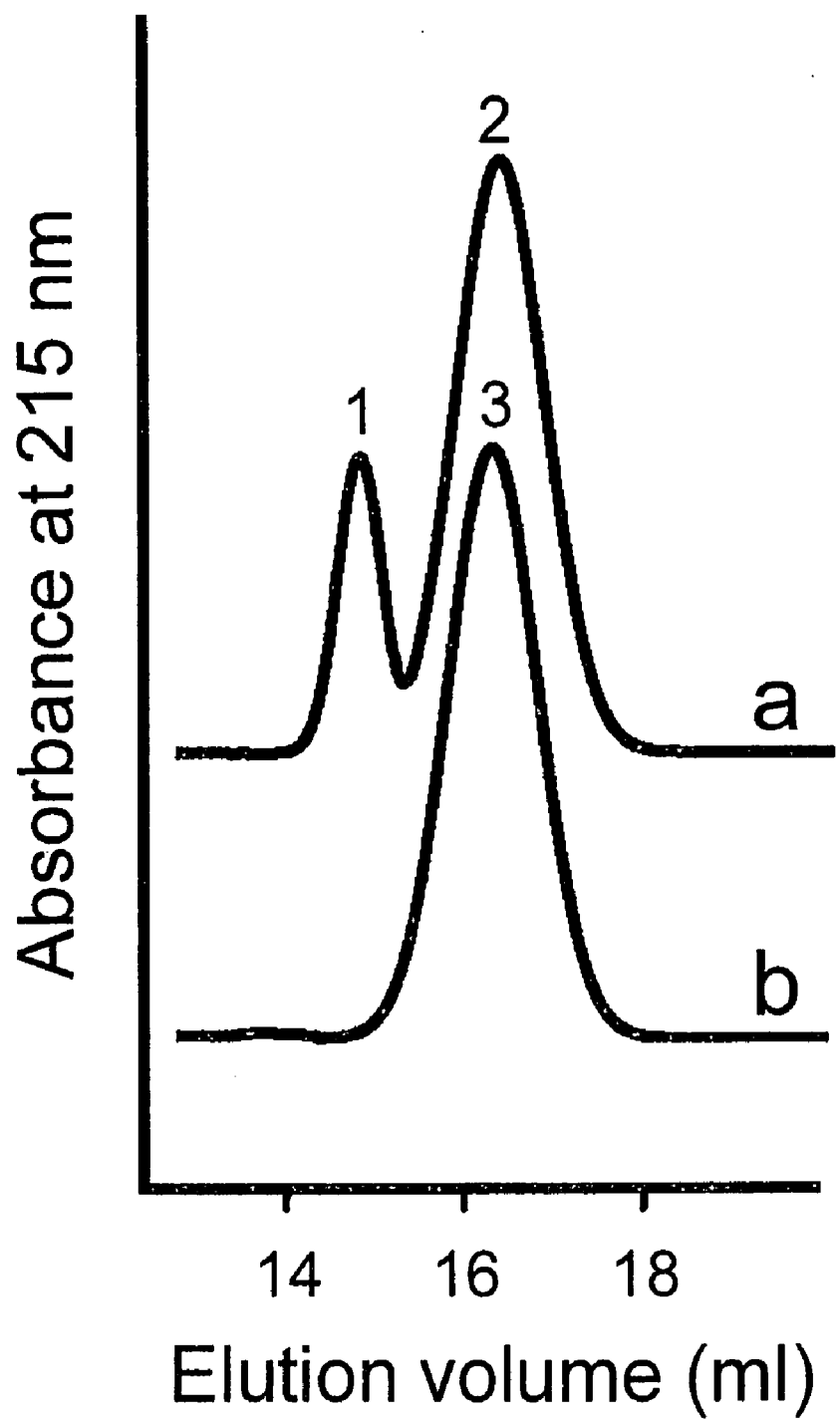
FIGS. 7A and 7B illustrate separation of minicollagen XXI species by gel filtration. 7A. Purified recombinant mC21, coexpressed in the P4H stably transfected *Drosophila* S2 cells, was separated by a Superdex 200 (HR 10/30) gel filtration column equilibrated with 0.1 M NaCl, 50 mM sodium acetate (pH 6.0), without prior denaturation (a), or after heating for 15 min in the presence of 5 mM DTT (dithiothreitol) (b). Flow rate, 0.4 ml/min. 7B. The different peak fractions (numbered 1 to 3 in 7A) were analyzed by SDS-PAGE under non-reducing conditions. Gel was visualized by silver nitrate staining. T, interchain disulfide-bonded trimers; D, interchain disulfide-bonded dimers; M, monomers.
Figure 7B:
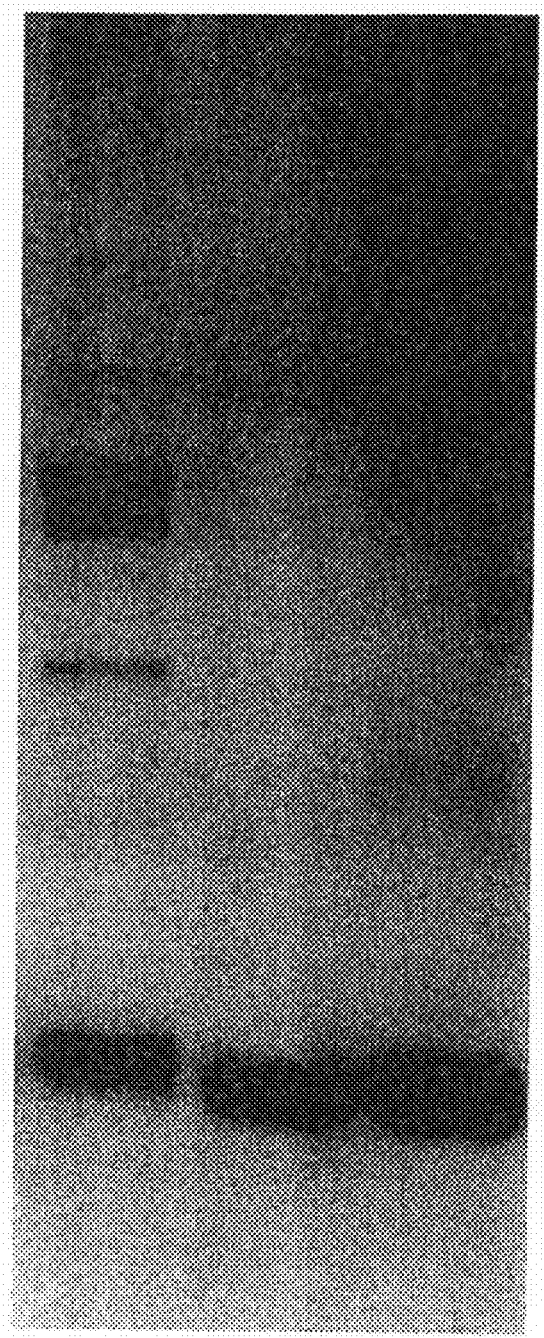

The presence of pepsin-resistant monomeric fragments (αCOL1) after pepsin digestion (FIG. 6, lanes 5 and 6) indicated that these monomers may originally derived from the triple-helical, non-interchain disulfide-bonded trimers, which were dissociated into single chains under SDS-PAGE. To demonstrate that mC21, coexpressed in the P4H stably transfected Drosophila S2 cells, contained nun-interchain disulfide-bonded trimers, a gel filtration column was used to separate different mC21 species. Purified recombinant mC21, coexpressed in the P4H stably transfected Drosophila S2 cells, was separated by a Superdex 200 (HR 10/30) gel filtration column equilibrated with 0.1 M NaCl, 50 mM sodium acetate (pH 6.0), without prior denaturation (FIG. 7A, a), or after heating for 15 min in the presence of 5 mM DTT (FIG. 7A, b). Flow rate, 0.4 ml/min. The mC21, coexpressed with P4H, was eluted as two peaks under native conditions (FIG. 7A, a). The different peak fractions (numbered 1 to 3 in 7A) were analyzed by SDS-PAGE under non-reducing conditions. Gel was visualized by silver nitrate staining. The results showed that the early peak fraction (peak 1) contained a mixture of interchain disulfide-bonded trimers, dimers and non-interchain disulfide-bonded monomers, while the later peak fraction (peak 2) contained non-interchain disulfide-bonded monomers only (FIG. 7B, lanes 1 and 2).

The monomers present in the early peak fraction co-eluted with the interchain disulfide-bonded trimers indicated that these monomeric species were derived from non-interchain disulfide-bonded trimers. After heating in the presence of dithiothreitol, the three chains dissociated and eluted in the later peak fraction (FIG. 7A, b, peak 3) and only monomers were seen (FIG. 7B, lane 3). It is concluded that the mC21 triple helices, coexpressed with P4H in the Drosophila S2 system, contained a mixture of interchain and non-interchain disulfide-bonded trimers.

While the invention has been described by way of example and in terms of preferred embodiment, it is to be understood that the invention is not limited thereto.

What is claimed is:

1. A method for producing a recombinant collagen comprising the steps of: providing a recombinant insect cell comprising a transfected polynucleotide encoding prolyl 4-hydroxylase, consisting of SEQ ID NOs:3 and 5; transfecting an expression vector comprising a recombinant collagen polynucleotide into the cell; culturing the cell under conditions such that the recombinant collagen polynucleotide is expressed; and recovering the expressed recombinant collagen.

2. The method as claimed in claim 1, wherein the cell is a *Trichoplusia ni* cell.

3. The method as claimed in claim 1, wherein the cell is a *Drosophila melanogaster* cell.

4. The method as claimed in claim 1, wherein the recombinant collagen polynucleotide encodes a collagenous (COL1) domain and a C-terminal noncollagenous (NC 1) domain of type XXI collagen consisting of SEQ ID NO: 1.

5. The method as claimed in claim 1, wherein the expressed recombinant collagen is secreted.

6. The method as claimed in claim 4, wherein the cell is a *Trichoplusia ni* cell.

7. The method as claimed in claim 4, wherein the cell is a *Drosophila melanogaster* cell.

8. The method as claimed in claim 4, wherein the expressed recombinant collagen is secreted.

* * * * *

SEQUENCE LISTING

```
<160> NUMBER OF SEQ ID NOS: 10

<210> SEQ ID NO 1
<211> LENGTH: 492
<212> TYPE: DNA
<213> ORGANISM: Artificial Sequence
<220> FEATURE:
<223> OTHER INFORMATION: Synthetic (NC1) domain of type XXI collagen
<220> FEATURE:
<221> NAME/KEY: CDS
<222> LOCATION: (1)..(492)

<400> SEQUENCE: 1 atg aag tta tgc ata tta ctg gcc gtc gtg gcc ttt gtt ggc ctc tcg     48
Met Lys Leu Cys Ile Leu Leu Ala Val Val Ala Phe Val Gly Leu Ser
1               5                   10                  15 ctc ggg aga tct att cct ggg cca cct ggt ccg ata ggc cca gag ggt     96
Leu Gly Arg Ser Ile Pro Gly Pro Pro Gly Pro Ile Gly Pro Glu Gly
            20                  25                  30 ccc aga gga tta cct ggt ttg cca gga aga gat ggt gtt cct gga tta    144
Pro Arg Gly Leu Pro Gly Leu Pro Gly Arg Asp Gly Val Pro Gly Leu
        35                  40                  45 gtg ggt gtc cct gga cgt cca ggt gtc aga gga tta aaa ggc cta cca    192
Val Gly Val Pro Gly Arg Pro Gly Val Arg Gly Leu Lys Gly Leu Pro
    50                  55                  60
```

```
gga aga aat ggg gaa aaa ggg agc caa ggg ttt ggg tat cct gga gaa    240
Gly Arg Asn Gly Glu Lys Gly Ser Gln Gly Phe Gly Tyr Pro Gly Glu
65                  70                  75                  80 caa ggt cct cct ggt ccc cca ggt cca gag ggc cct cct gga ata agc    288
Gln Gly Pro Pro Gly Pro Pro Gly Pro Glu Gly Pro Pro Gly Ile Ser
                85                  90                  95 aaa gaa ggt cct cca gga gac cca ggt ctc cct ggc aaa gat gga gac    336
Lys Glu Gly Pro Pro Gly Asp Pro Gly Leu Pro Gly Lys Asp Gly Asp
            100                 105                 110 cat gga aaa cct gga atc caa ggg caa cca ggc ccc cca ggc atc tgc    384
His Gly Lys Pro Gly Ile Gln Gly Gln Pro Gly Pro Pro Gly Ile Cys
        115                 120                 125 gac cca tca cta tgt ttt agt gta att gcc aga aga gat ccg ttc aga    432
Asp Pro Ser Leu Cys Phe Ser Val Ile Ala Arg Arg Asp Pro Phe Arg
130                 135                 140 aaa gga cca aac tat agt cta gac gac agc agc cat cat cac cat cac    480
Lys Gly Pro Asn Tyr Ser Leu Asp Asp Ser Ser His His His His His
145                 150                 155                 160 cat agc agc ggc                                                    492
His Ser Ser Gly <210> SEQ ID NO 2
<211> LENGTH: 164
<212> TYPE: PRT
<213> ORGANISM: Artificial Sequence
<220> FEATURE:
<223> OTHER INFORMATION: Synthetic recombinant mC21 (XXI) amino acid
      sequence

<400> SEQUENCE: 2

Met Lys Leu Cys Ile Leu Leu Ala Val Val Ala Phe Val Gly Leu Ser
1               5                   10                  15

Leu Gly Arg Ser Ile Pro Gly Pro Pro Gly Pro Ile Gly Pro Glu Gly
                20                  25                  30

Pro Arg Gly Leu Pro Gly Leu Pro Gly Arg Asp Gly Val Pro Gly Leu
            35                  40                  45

Val Gly Val Pro Gly Arg Pro Gly Val Arg Gly Leu Lys Gly Leu Pro
50                  55                  60

Gly Arg Asn Gly Glu Lys Gly Ser Gln Gly Phe Gly Tyr Pro Gly Glu
65                  70                  75                  80

Gln Gly Pro Pro Gly Pro Pro Gly Pro Glu Gly Pro Pro Gly Ile Ser
                85                  90                  95

Lys Glu Gly Pro Pro Gly Asp Pro Gly Leu Pro Gly Lys Asp Gly Asp
            100                 105                 110

His Gly Lys Pro Gly Ile Gln Gly Gln Pro Gly Pro Pro Gly Ile Cys
        115                 120                 125

Asp Pro Ser Leu Cys Phe Ser Val Ile Ala Arg Arg Asp Pro Phe Arg
130                 135                 140

Lys Gly Pro Asn Tyr Ser Leu Asp Asp Ser Ser His His His His His
145                 150                 155                 160

His Ser Ser Gly

<210> SEQ ID NO 3
<211> LENGTH: 1602
<212> TYPE: DNA
<213> ORGANISM: Homo sapiens
<220> FEATURE:
<221> NAME/KEY: CDS
<222> LOCATION: (1)..(1602)
```

<223> OTHER INFORMATION: human prolyl 4-hydroxylase alpha subunit

<400> SEQUENCE: 3

| | | | | | | | | | | | | | | | | |
|---|---|---|---|---|---|---|---|---|---|---|---|---|---|---|---|---|
| atg | gtc | tgg | tat | ata | tta | att | ata | gga | att | ctg | ctt | ccc | cag | tct | ttg | 48 |
| Met | Val | Trp | Tyr | Ile | Leu | Ile | Ile | Gly | Ile | Leu | Leu | Pro | Gln | Ser | Leu | |
| 1 | | | | 5 | | | | | 10 | | | | | 15 | | |

| gct | cat | cca | ggc | ttt | ttt | act | tca | att | ggt | cag | atg | act | gat | ttg | atc | 96 |
|---|---|---|---|---|---|---|---|---|---|---|---|---|---|---|---|---|
| Ala | His | Pro | Gly | Phe | Phe | Thr | Ser | Ile | Gly | Gln | Met | Thr | Asp | Leu | Ile | |
| | | | 20 | | | | | 25 | | | | | 30 | | | |

| cat | act | gag | aaa | gat | ctg | gtg | act | tct | ctg | aaa | gat | tat | att | aag | gca | 144 |
|---|---|---|---|---|---|---|---|---|---|---|---|---|---|---|---|---|
| His | Thr | Glu | Lys | Asp | Leu | Val | Thr | Ser | Leu | Lys | Asp | Tyr | Ile | Lys | Ala | |
| | | 35 | | | | | 40 | | | | | 45 | | | | |

| gaa | gag | gac | aag | tta | gaa | caa | ata | aaa | aaa | tgg | gca | gag | aag | tta | gat | 192 |
|---|---|---|---|---|---|---|---|---|---|---|---|---|---|---|---|---|
| Glu | Glu | Asp | Lys | Leu | Glu | Gln | Ile | Lys | Lys | Trp | Ala | Glu | Lys | Leu | Asp | |
| 50 | | | | | 55 | | | | | 60 | | | | | | |

| cgg | cta | act | agt | aca | gcg | aca | aaa | gat | cca | gaa | gga | ttt | gtt | ggg | cat | 240 |
|---|---|---|---|---|---|---|---|---|---|---|---|---|---|---|---|---|
| Arg | Leu | Thr | Ser | Thr | Ala | Thr | Lys | Asp | Pro | Glu | Gly | Phe | Val | Gly | His | |
| 65 | | | | 70 | | | | | 75 | | | | | 80 | | |

| cca | gta | aat | gca | ttc | aaa | tta | atg | aaa | cgt | ctg | aat | act | gag | tgg | agt | 288 |
|---|---|---|---|---|---|---|---|---|---|---|---|---|---|---|---|---|
| Pro | Val | Asn | Ala | Phe | Lys | Leu | Met | Lys | Arg | Leu | Asn | Thr | Glu | Trp | Ser | |
| | | | | 85 | | | | | 90 | | | | | 95 | | |

| gag | ttg | gag | aat | ctg | gtc | ctt | aag | gat | atg | tca | gat | ggc | ttt | atc | tct | 336 |
|---|---|---|---|---|---|---|---|---|---|---|---|---|---|---|---|---|
| Glu | Leu | Glu | Asn | Leu | Val | Leu | Lys | Asp | Met | Ser | Asp | Gly | Phe | Ile | Ser | |
| | | | | 100 | | | | | 105 | | | | | 110 | | |

| aac | cta | acc | att | cag | aga | cca | gta | ctt | tct | aat | gat | gaa | gat | cag | gtt | 384 |
|---|---|---|---|---|---|---|---|---|---|---|---|---|---|---|---|---|
| Asn | Leu | Thr | Ile | Gln | Arg | Pro | Val | Leu | Ser | Asn | Asp | Glu | Asp | Gln | Val | |
| | | | 115 | | | | | 120 | | | | | 125 | | | |

| ggg | gca | gcc | aaa | gct | ctg | tta | cgt | ctc | cag | gat | acc | tac | aat | ttg | gat | 432 |
|---|---|---|---|---|---|---|---|---|---|---|---|---|---|---|---|---|
| Gly | Ala | Ala | Lys | Ala | Leu | Leu | Arg | Leu | Gln | Asp | Thr | Tyr | Asn | Leu | Asp | |
| | | 130 | | | | | 135 | | | | | 140 | | | | |

| aca | gat | acc | atc | tca | aag | ggt | aat | ctt | cca | gga | gtg | aaa | cac | aaa | tct | 480 |
|---|---|---|---|---|---|---|---|---|---|---|---|---|---|---|---|---|
| Thr | Asp | Thr | Ile | Ser | Lys | Gly | Asn | Leu | Pro | Gly | Val | Lys | His | Lys | Ser | |
| 145 | | | | | 150 | | | | | 155 | | | | | 160 | |

| ttt | cta | acg | gct | gag | gac | tgc | ttt | gag | ttg | ggc | aaa | gtg | gcc | tat | aca | 528 |
|---|---|---|---|---|---|---|---|---|---|---|---|---|---|---|---|---|
| Phe | Leu | Thr | Ala | Glu | Asp | Cys | Phe | Glu | Leu | Gly | Lys | Val | Ala | Tyr | Thr | |
| | | | | 165 | | | | | 170 | | | | | 175 | | |

| gaa | gca | gat | tat | tac | cat | acg | gaa | ctg | tgg | atg | gaa | caa | gcc | cta | agg | 576 |
|---|---|---|---|---|---|---|---|---|---|---|---|---|---|---|---|---|
| Glu | Ala | Asp | Tyr | Tyr | His | Thr | Glu | Leu | Trp | Met | Glu | Gln | Ala | Leu | Arg | |
| | | | | 180 | | | | | 185 | | | | | 190 | | |

| caa | ctg | gat | gaa | ggc | gag | att | tct | acc | ata | gat | aaa | gtc | tct | gtt | cta | 624 |
|---|---|---|---|---|---|---|---|---|---|---|---|---|---|---|---|---|
| Gln | Leu | Asp | Glu | Gly | Glu | Ile | Ser | Thr | Ile | Asp | Lys | Val | Ser | Val | Leu | |
| | | | 195 | | | | | 200 | | | | | 205 | | | |

| gat | tat | ttg | agc | tat | gcg | gta | tat | cag | cag | gga | gac | ctg | gat | aag | gca | 672 |
|---|---|---|---|---|---|---|---|---|---|---|---|---|---|---|---|---|
| Asp | Tyr | Leu | Ser | Tyr | Ala | Val | Tyr | Gln | Gln | Gly | Asp | Leu | Asp | Lys | Ala | |
| 210 | | | | | 215 | | | | | 220 | | | | | | |

| ctt | ttg | ctc | aca | aag | aag | ctt | ctt | gaa | cta | gat | cct | gaa | cat | cag | agg | 720 |
|---|---|---|---|---|---|---|---|---|---|---|---|---|---|---|---|---|
| Leu | Leu | Leu | Thr | Lys | Lys | Leu | Leu | Glu | Leu | Asp | Pro | Glu | His | Gln | Arg | |
| 225 | | | | 230 | | | | | 235 | | | | | 240 | | |

| gct | aat | ggt | aac | tta | aaa | tat | ttt | gag | tat | ata | atg | gct | aaa | gaa | aaa | 768 |
|---|---|---|---|---|---|---|---|---|---|---|---|---|---|---|---|---|
| Ala | Asn | Gly | Asn | Leu | Lys | Tyr | Phe | Glu | Tyr | Ile | Met | Ala | Lys | Glu | Lys | |
| | | | | 245 | | | | | 250 | | | | | 255 | | |

| gat | gtc | aat | aag | tct | gct | tca | gat | gac | caa | tct | gat | cag | aaa | act | aca | 816 |
|---|---|---|---|---|---|---|---|---|---|---|---|---|---|---|---|---|
| Asp | Val | Asn | Lys | Ser | Ala | Ser | Asp | Asp | Gln | Ser | Asp | Gln | Lys | Thr | Thr | |
| | | | 260 | | | | | 265 | | | | | 270 | | | |

| cca | aag | aaa | aaa | ggg | gtt | gct | gtg | gat | tac | ctg | cca | gag | aga | cag | aag | 864 |
|---|---|---|---|---|---|---|---|---|---|---|---|---|---|---|---|---|
| Pro | Lys | Lys | Lys | Gly | Val | Ala | Val | Asp | Tyr | Leu | Pro | Glu | Arg | Gln | Lys | |
| | | 275 | | | | | 280 | | | | | 285 | | | | |

| tac | gaa | atg | ctg | tgc | cgt | ggg | gag | ggt | atc | aaa | atg | acc | cct | cgg | aga | 912 |
|---|---|---|---|---|---|---|---|---|---|---|---|---|---|---|---|---|
| Tyr | Glu | Met | Leu | Cys | Arg | Gly | Glu | Gly | Ile | Lys | Met | Thr | Pro | Arg | Arg | |
| | 290 | | | | | 295 | | | | | 300 | | | | | |

```
cag aaa aaa ctc ttt tgc cgc tgc cat gat gga aac cgt aat cct aaa      960
Gln Lys Lys Leu Phe Cys Arg Cys His Asp Gly Asn Arg Asn Pro Lys
305                 310                 315                 320 ttt att ctg gct cca gct aaa cag gag gat gaa tgg gac aag cct cgt     1008
Phe Ile Leu Ala Pro Ala Lys Gln Glu Asp Glu Trp Asp Lys Pro Arg
                325                 330                 335 att att cgc ttc cat gat att att tct gat gca gaa att gaa atc gtc     1056
Ile Ile Arg Phe His Asp Ile Ile Ser Asp Ala Glu Ile Glu Ile Val
            340                 345                 350 aaa gac cta gca aaa cca agg ctg agg cga gcc acc att tca aac cca     1104
Lys Asp Leu Ala Lys Pro Arg Leu Arg Arg Ala Thr Ile Ser Asn Pro
        355                 360                 365 ata gca gga gac ttg gag acg gta cat tac aga att agc aaa agt gcc     1152
Ile Ala Gly Asp Leu Glu Thr Val His Tyr Arg Ile Ser Lys Ser Ala
    370                 375                 380 tgg ctc tct ggc tat gaa aat cct gtg gtg tct cga att aat atg aga     1200
Trp Leu Ser Gly Tyr Glu Asn Pro Val Val Ser Arg Ile Asn Met Arg
385                 390                 395                 400 ata caa gat cta aca gga cta gat gtt tcc aca gca gag gaa tta cag     1248
Ile Gln Asp Leu Thr Gly Leu Asp Val Ser Thr Ala Glu Glu Leu Gln
                405                 410                 415 gta gca aat tat gga gtt gga gga cag tat gaa ccc cat ttt gac ttt     1296
Val Ala Asn Tyr Gly Val Gly Gly Gln Tyr Glu Pro His Phe Asp Phe
            420                 425                 430 gca cgg aaa gat gag cca gat gct ttc aaa gag ctg ggg aca gga aat     1344
Ala Arg Lys Asp Glu Pro Asp Ala Phe Lys Glu Leu Gly Thr Gly Asn
        435                 440                 445 aga att gct aca tgg ctg ttt tat atg agt gat gtg tct gca gga gga     1392
Arg Ile Ala Thr Trp Leu Phe Tyr Met Ser Asp Val Ser Ala Gly Gly
    450                 455                 460 gcc act gtt ttt cct gaa gtt gga gct agt gtt tgg ccc aaa aaa gga     1440
Ala Thr Val Phe Pro Glu Val Gly Ala Ser Val Trp Pro Lys Lys Gly
465                 470                 475                 480 act gct gtt ttc tgg tat aat ctg ttt gcc agt gga gaa gga gat tat     1488
Thr Ala Val Phe Trp Tyr Asn Leu Phe Ala Ser Gly Glu Gly Asp Tyr
                485                 490                 495 agt aca cgg cat gca gcc tgt cca gtg cta gtt ggc aac aaa tgg gta     1536
Ser Thr Arg His Ala Ala Cys Pro Val Leu Val Gly Asn Lys Trp Val
            500                 505                 510 tcc aat aaa tgg ctc cat gaa cgt gga caa gaa ttt cga aga cct tgt     1584
Ser Asn Lys Trp Leu His Glu Arg Gly Gln Glu Phe Arg Arg Pro Cys
        515                 520                 525 acg ttg tca gaa ttg gaa                                             1602
Thr Leu Ser Glu Leu Glu
    530

<210> SEQ ID NO 4
<211> LENGTH: 534
<212> TYPE: PRT
<213> ORGANISM: Homo sapiens

<400> SEQUENCE: 4

Met Val Trp Tyr Ile Leu Ile Ile Gly Ile Leu Leu Pro Gln Ser Leu
1               5                   10                  15

Ala His Pro Gly Phe Phe Thr Ser Ile Gly Gln Met Thr Asp Leu Ile
                20                  25                  30

His Thr Glu Lys Asp Leu Val Thr Ser Leu Lys Asp Tyr Ile Lys Ala
            35                  40                  45

Glu Glu Asp Lys Leu Glu Gln Ile Lys Lys Trp Ala Glu Lys Leu Asp
```

```
        50                  55                  60
Arg Leu Thr Ser Thr Ala Thr Lys Asp Pro Glu Gly Phe Val Gly His
 65                  70                  75                  80

Pro Val Asn Ala Phe Lys Leu Met Lys Arg Leu Asn Thr Glu Trp Ser
                 85                  90                  95

Glu Leu Glu Asn Leu Val Leu Lys Asp Met Ser Asp Gly Phe Ile Ser
                100                 105                 110

Asn Leu Thr Ile Gln Arg Pro Val Leu Ser Asn Asp Glu Asp Gln Val
                115                 120                 125

Gly Ala Ala Lys Ala Leu Leu Arg Leu Gln Asp Thr Tyr Asn Leu Asp
130                 135                 140

Thr Asp Thr Ile Ser Lys Gly Asn Leu Pro Gly Val Lys His Lys Ser
145                 150                 155                 160

Phe Leu Thr Ala Glu Asp Cys Phe Glu Leu Gly Lys Val Ala Tyr Thr
                165                 170                 175

Glu Ala Asp Tyr Tyr His Thr Glu Leu Trp Met Glu Gln Ala Leu Arg
                180                 185                 190

Gln Leu Asp Glu Gly Glu Ile Ser Thr Ile Asp Lys Val Ser Val Leu
                195                 200                 205

Asp Tyr Leu Ser Tyr Ala Val Tyr Gln Gln Gly Asp Leu Asp Lys Ala
210                 215                 220

Leu Leu Leu Thr Lys Lys Leu Leu Glu Leu Asp Pro Glu His Gln Arg
225                 230                 235                 240

Ala Asn Gly Asn Leu Lys Tyr Phe Glu Tyr Ile Met Ala Lys Glu Lys
                245                 250                 255

Asp Val Asn Lys Ser Ala Ser Asp Gln Ser Asp Gln Lys Thr Thr
                260                 265                 270

Pro Lys Lys Lys Gly Val Ala Val Asp Tyr Leu Pro Glu Arg Gln Lys
                275                 280                 285

Tyr Glu Met Leu Cys Arg Gly Glu Gly Ile Lys Met Thr Pro Arg Arg
                290                 295                 300

Gln Lys Lys Leu Phe Cys Arg Cys His Asp Gly Asn Arg Asn Pro Lys
305                 310                 315                 320

Phe Ile Leu Ala Pro Ala Lys Gln Glu Asp Glu Trp Asp Lys Pro Arg
                325                 330                 335

Ile Ile Arg Phe His Asp Ile Ile Ser Asp Ala Glu Ile Glu Ile Val
                340                 345                 350

Lys Asp Leu Ala Lys Pro Arg Leu Arg Arg Ala Thr Ile Ser Asn Pro
                355                 360                 365

Ile Ala Gly Asp Leu Glu Thr Val His Tyr Arg Ile Ser Lys Ser Ala
                370                 375                 380

Trp Leu Ser Gly Tyr Glu Asn Pro Val Val Ser Arg Ile Asn Met Arg
385                 390                 395                 400

Ile Gln Asp Leu Thr Gly Leu Asp Val Ser Thr Ala Glu Glu Leu Gln
                405                 410                 415

Val Ala Asn Tyr Gly Val Gly Gly Gln Tyr Glu Pro His Phe Asp Phe
                420                 425                 430

Ala Arg Lys Asp Glu Pro Asp Ala Phe Lys Glu Leu Gly Thr Gly Asn
                435                 440                 445

Arg Ile Ala Thr Trp Leu Phe Tyr Met Ser Asp Val Ser Ala Gly Gly
                450                 455                 460

Ala Thr Val Phe Pro Glu Val Gly Ala Ser Val Trp Pro Lys Lys Gly
465                 470                 475                 480
```

```
Thr Ala Val Phe Trp Tyr Asn Leu Phe Ala Ser Gly Glu Gly Asp Tyr
            485                 490                 495

Ser Thr Arg His Ala Ala Cys Pro Val Leu Val Gly Asn Lys Trp Val
        500                 505                 510

Ser Asn Lys Trp Leu His Glu Arg Gly Gln Glu Phe Arg Arg Pro Cys
    515                 520                 525

Thr Leu Ser Glu Leu Glu
    530

<210> SEQ ID NO 5
<211> LENGTH: 1524
<212> TYPE: DNA
<213> ORGANISM: Homo sapiens
<220> FEATURE:
<221> NAME/KEY: CDS
<222> LOCATION: (1)..(1524)
<223> OTHER INFORMATION: human prolyl 4-hydroxylase beta subunit

<400> SEQUENCE: 5 atg gtg cgc cgc gct ctg ctg tgc ctg ccg tgg acc gcc ctg gtg cgc      48
Met Val Arg Arg Ala Leu Leu Cys Leu Pro Trp Thr Ala Leu Val Arg
1               5                   10                  15 gcc gac gcc ccc gag gag gag gac cac gtc ctg gtg ctg cgg aaa agc      96
Ala Asp Ala Pro Glu Glu Glu Asp His Val Leu Val Leu Arg Lys Ser
            20                  25                  30 aac ttc gcg gag gcg ctg gcg gcc cac aag tac ctg ctg gtg gag ttc     144
Asn Phe Ala Glu Ala Leu Ala Ala His Lys Tyr Leu Leu Val Glu Phe
        35                  40                  45 tat gcc cct tgg tgt ggc cac tgc aag gct ctg gcc cct gag tat gcc     192
Tyr Ala Pro Trp Cys Gly His Cys Lys Ala Leu Ala Pro Glu Tyr Ala
    50                  55                  60 aaa gcc gct ggg aag ctg aag gca gaa ggt tcc gag atc agg ttg gcc     240
Lys Ala Ala Gly Lys Leu Lys Ala Glu Gly Ser Glu Ile Arg Leu Ala
65                  70                  75                  80 aag gtg gac gcc acg gag gag tct gac cta gcc cag cag tac ggc gtg     288
Lys Val Asp Ala Thr Glu Glu Ser Asp Leu Ala Gln Gln Tyr Gly Val
                85                  90                  95 cgc ggc tat ccc acc atc aag ttc ttc agg aat gga gac acg gct tcc     336
Arg Gly Tyr Pro Thr Ile Lys Phe Phe Arg Asn Gly Asp Thr Ala Ser
            100                 105                 110 ccc aag gaa tat aca gct ggc aga gag gct gat gac atc gtg aac tgg     384
Pro Lys Glu Tyr Thr Ala Gly Arg Glu Ala Asp Asp Ile Val Asn Trp
        115                 120                 125 ctg aag aag cgc acg ggc ccg gct gcc acc acc ctg cct gac ggc gca     432
Leu Lys Lys Arg Thr Gly Pro Ala Ala Thr Thr Leu Pro Asp Gly Ala
    130                 135                 140 gct gca gag tcc ttg gtg gag tcc agc gag gtg gct gtc atc ggc ttc     480
Ala Ala Glu Ser Leu Val Glu Ser Ser Glu Val Ala Val Ile Gly Phe
145                 150                 155                 160 ttc aag gac gtg gag tcg gac tct gcc aag cag ttt ttg cag gca gca     528
Phe Lys Asp Val Glu Ser Asp Ser Ala Lys Gln Phe Leu Gln Ala Ala
                165                 170                 175 gag gcc atc gat gac ata cca ttt ggg atc act tcc aac agt gac gtg     576
Glu Ala Ile Asp Asp Ile Pro Phe Gly Ile Thr Ser Asn Ser Asp Val
            180                 185                 190 ttc tcc aaa tac cag ctc gac aaa gat ggg gtt gtc ctc ttt aag aag     624
Phe Ser Lys Tyr Gln Leu Asp Lys Asp Gly Val Val Leu Phe Lys Lys
        195                 200                 205 ttt gat gaa ggc cgg aac aac ttt gaa ggg gag gtc acc aag gag aac     672
Phe Asp Glu Gly Arg Asn Asn Phe Glu Gly Glu Val Thr Lys Glu Asn
```

```
        210                 215                 220
ctg ctg gac ttt atc aaa cac aac cag ctg ccc ctt gtc atc gag ttc    720
Leu Leu Asp Phe Ile Lys His Asn Gln Leu Pro Leu Val Ile Glu Phe
225                 230                 235                 240 acc gag cag aca gcc ccg aag att ttt gga ggt gaa atc aag act cac    768
Thr Glu Gln Thr Ala Pro Lys Ile Phe Gly Gly Glu Ile Lys Thr His
                245                 250                 255 atc ctg ctg ttc ttg ccc aag agt gtg tct gac tat gac ggc aaa ctg    816
Ile Leu Leu Phe Leu Pro Lys Ser Val Ser Asp Tyr Asp Gly Lys Leu
        260                 265                 270 agc aac ttc aaa aca gca gcc gag agc ttc aag ggc aag atc ctg ttc    864
Ser Asn Phe Lys Thr Ala Ala Glu Ser Phe Lys Gly Lys Ile Leu Phe
            275                 280                 285 atc ttc atc gac agc gac cac acc gac aac cag cgc atc ctc gag ttc    912
Ile Phe Ile Asp Ser Asp His Thr Asp Asn Gln Arg Ile Leu Glu Phe
                290                 295                 300 ttt ggc ctg aag aag gaa gag tgc ccg gcc gtg cgc ctc atc acc ctg    960
Phe Gly Leu Lys Lys Glu Glu Cys Pro Ala Val Arg Leu Ile Thr Leu
305                 310                 315                 320 gag gag gag atg acc aag tac aag ccc gaa tcg gag gag ctg acg gca    1008
Glu Glu Glu Met Thr Lys Tyr Lys Pro Glu Ser Glu Glu Leu Thr Ala
                325                 330                 335 gag agg atc aca gag ttc tgc cac cgc ttc ctg gag ggc aaa atc aag    1056
Glu Arg Ile Thr Glu Phe Cys His Arg Phe Leu Glu Gly Lys Ile Lys
            340                 345                 350 ccc cac ctg atg agc cag gag ctg ccg gag gac tgg gac aag cag cct    1104
Pro His Leu Met Ser Gln Glu Leu Pro Glu Asp Trp Asp Lys Gln Pro
                355                 360                 365 gtc aag gtg ctt gtt ggg aag aac ttt gaa gac gtg gct ttt gat gaa    1152
Val Lys Val Leu Val Gly Lys Asn Phe Glu Asp Val Ala Phe Asp Glu
370                 375                 380 aaa aaa aac gtc ttt gtg gag ttc tat gcc cca tgg tgt ggt cac tgc    1200
Lys Lys Asn Val Phe Val Glu Phe Tyr Ala Pro Trp Cys Gly His Cys
                385                 390                 395                 400 aaa cag ttg gct ccc att tgg gat aaa ctg gga gag acg tac aag gac    1248
Lys Gln Leu Ala Pro Ile Trp Asp Lys Leu Gly Glu Thr Tyr Lys Asp
            405                 410                 415 cat gag aac atc gtc atc gcc aag atg gac tcg act gcc aac gag gtg    1296
His Glu Asn Ile Val Ile Ala Lys Met Asp Ser Thr Ala Asn Glu Val
                420                 425                 430 gag gcc gtc aaa gtg cac agc ttc ccc aca ctc aag ttc ttt cct gcc    1344
Glu Ala Val Lys Val His Ser Phe Pro Thr Leu Lys Phe Phe Pro Ala
            435                 440                 445 agt gcc gac agg acg gtc att gat tac aac ggg gaa cgc acg ctg gat    1392
Ser Ala Asp Arg Thr Val Ile Asp Tyr Asn Gly Glu Arg Thr Leu Asp
450                 455                 460 ggt ttt aag aaa ttc ctg gag agc ggt ggc caa gat ggg gca ggg ggt    1440
Gly Phe Lys Lys Phe Leu Glu Ser Gly Gly Gln Asp Gly Ala Gly Gly
465                 470                 475                 480 gat gac gat ctc gag gac ctg gaa gaa gca gag gag cca gac atg gag    1488
Asp Asp Asp Leu Glu Asp Leu Glu Glu Ala Glu Glu Pro Asp Met Glu
                485                 490                 495 gaa gac gat gat cag aaa gct gtg aaa gat gaa ctg                    1524
Glu Asp Asp Asp Gln Lys Ala Val Lys Asp Glu Leu
                500                 505

<210> SEQ ID NO 6
<211> LENGTH: 508
<212> TYPE: PRT
<213> ORGANISM: Homo sapiens
```

<400> SEQUENCE: 6

```
Met Val Arg Arg Ala Leu Leu Cys Leu Pro Trp Thr Ala Leu Val Arg
1               5                   10                  15

Ala Asp Ala Pro Glu Glu Glu Asp His Val Leu Val Leu Arg Lys Ser
            20                  25                  30

Asn Phe Ala Glu Ala Leu Ala Ala His Lys Tyr Leu Leu Val Glu Phe
        35                  40                  45

Tyr Ala Pro Trp Cys Gly His Cys Lys Ala Leu Ala Pro Glu Tyr Ala
    50                  55                  60

Lys Ala Ala Gly Lys Leu Lys Ala Glu Gly Ser Glu Ile Arg Leu Ala
65                  70                  75                  80

Lys Val Asp Ala Thr Glu Glu Ser Asp Leu Ala Gln Gln Tyr Gly Val
                85                  90                  95

Arg Gly Tyr Pro Thr Ile Lys Phe Phe Arg Asn Gly Asp Thr Ala Ser
            100                 105                 110

Pro Lys Glu Tyr Thr Ala Gly Arg Glu Ala Asp Asp Ile Val Asn Trp
        115                 120                 125

Leu Lys Lys Arg Thr Gly Pro Ala Ala Thr Thr Leu Pro Asp Gly Ala
130                 135                 140

Ala Ala Glu Ser Leu Val Glu Ser Ser Glu Val Ala Val Ile Gly Phe
145                 150                 155                 160

Phe Lys Asp Val Glu Ser Asp Ser Ala Lys Gln Phe Leu Gln Ala Ala
                165                 170                 175

Glu Ala Ile Asp Asp Ile Pro Phe Gly Ile Thr Ser Asn Ser Asp Val
            180                 185                 190

Phe Ser Lys Tyr Gln Leu Asp Lys Asp Gly Val Val Leu Phe Lys Lys
        195                 200                 205

Phe Asp Glu Gly Arg Asn Asn Phe Glu Gly Glu Val Thr Lys Glu Asn
    210                 215                 220

Leu Leu Asp Phe Ile Lys His Asn Gln Leu Pro Leu Val Ile Glu Phe
225                 230                 235                 240

Thr Glu Gln Thr Ala Pro Lys Ile Phe Gly Gly Glu Ile Lys Thr His
                245                 250                 255

Ile Leu Leu Phe Leu Pro Lys Ser Val Ser Asp Tyr Asp Gly Lys Leu
            260                 265                 270

Ser Asn Phe Lys Thr Ala Ala Glu Ser Phe Lys Gly Lys Ile Leu Phe
        275                 280                 285

Ile Phe Ile Asp Ser Asp His Thr Asp Asn Gln Arg Ile Leu Glu Phe
    290                 295                 300

Phe Gly Leu Lys Lys Glu Glu Cys Pro Ala Val Arg Leu Ile Thr Leu
305                 310                 315                 320

Glu Glu Glu Met Thr Lys Tyr Lys Pro Glu Ser Glu Glu Leu Thr Ala
                325                 330                 335

Glu Arg Ile Thr Glu Phe Cys His Arg Phe Leu Glu Gly Lys Ile Lys
            340                 345                 350

Pro His Leu Met Ser Gln Glu Leu Pro Glu Asp Trp Asp Lys Gln Pro
        355                 360                 365

Val Lys Val Leu Val Gly Lys Asn Phe Glu Asp Val Ala Phe Asp Glu
    370                 375                 380

Lys Lys Asn Val Phe Val Glu Phe Tyr Ala Pro Trp Cys Gly His Cys
385                 390                 395                 400

Lys Gln Leu Ala Pro Ile Trp Asp Lys Leu Gly Glu Thr Tyr Lys Asp
```

```
                    405                 410                 415
His Glu Asn Ile Val Ile Ala Lys Met Asp Ser Thr Ala Asn Glu Val
            420                 425                 430

Glu Ala Val Lys Val His Ser Phe Pro Thr Leu Lys Phe Phe Pro Ala
        435                 440                 445

Ser Ala Asp Arg Thr Val Ile Asp Tyr Asn Gly Glu Arg Thr Leu Asp
    450                 455                 460

Gly Phe Lys Lys Phe Leu Glu Ser Gly Gly Gln Asp Gly Ala Gly Gly
465                 470                 475                 480

Asp Asp Asp Leu Glu Asp Leu Glu Glu Ala Glu Glu Pro Asp Met Glu
            485                 490                 495

Glu Asp Asp Asp Gln Lys Ala Val Lys Asp Glu Leu
            500                 505

<210> SEQ ID NO 7
<211> LENGTH: 19
<212> TYPE: DNA
<213> ORGANISM: Artificial Sequence
<220> FEATURE:
<223> OTHER INFORMATION: forward primer for amplifying human prolyl
      4-hydroxylase a subunit

<400> SEQUENCE: 7
atcgattatc atgtctgga                                                   19

<210> SEQ ID NO 8
<211> LENGTH: 19
<212> TYPE: DNA
<213> ORGANISM: Artificial Sequence
<220> FEATURE:
<223> OTHER INFORMATION: reverse primer for amplifying human prolyl
      4-hydroxylase a subunit

<400> SEQUENCE: 8
ctttgagtga gcatcgatc                                                   19

<210> SEQ ID NO 9
<211> LENGTH: 33
<212> TYPE: DNA
<213> ORGANISM: Artificial Sequence
<220> FEATURE:
<223> OTHER INFORMATION: forward primer for amplifying COL21A1

<400> SEQUENCE: 9
ttagatctat tcctgggcca cctggtccga tag                                   33

<210> SEQ ID NO 10
<211> LENGTH: 30
<212> TYPE: DNA
<213> ORGANISM: Artificial Sequence
<220> FEATURE:
<223> OTHER INFORMATION: reverse primer for amplifying COL21A1

<400> SEQUENCE: 10
aatctagact aatagtttgg tcctttctg                                        30
```